United States Patent
Gillespie et al.

(10) Patent No.: US 8,795,350 B2
(45) Date of Patent: Aug. 5, 2014

(54) FENESTRATED ENDOGRAFT

(75) Inventors: David L. Gillespie, Rochester, NY (US); Doran Mix, Rochester, NY (US)

(73) Assignee: University of Rochester, Rochester, NY (US)

( * ) Notice: Subject to any disclaimer, the term of this patent is extended or adjusted under 35 U.S.C. 154(b) by 50 days.

(21) Appl. No.: 13/396,523

(22) Filed: Feb. 14, 2012

(65) Prior Publication Data

US 2012/0209369 A1 Aug. 16, 2012

Related U.S. Application Data

(60) Provisional application No. 61/442,633, filed on Feb. 14, 2011.

(51) Int. Cl.
*A61F 2/06* (2013.01)

(52) U.S. Cl.
USPC .......................................... 623/1.13

(58) Field of Classification Search
USPC ............. 623/1.1, 1.13, 1.14, 1.15, 1.16, 1.17, 623/1.18, 1.19, 1.2, 1.21, 1.23
See application file for complete search history.

(56) References Cited

U.S. PATENT DOCUMENTS

| | | | |
|---|---|---|---|
| 5,669,924 A | 9/1997 | Shaknovich | |
| 6,149,682 A | 11/2000 | Frid | |
| 7,105,019 B2 | 9/2006 | Hojeibane | |
| 2003/0195606 A1 | 10/2003 | Davidson et al. | |
| 2004/0034406 A1* | 2/2004 | Thramann | 623/1.13 |
| 2004/0172126 A1 | 9/2004 | Hojeibane | |
| 2008/0103587 A1 | 5/2008 | Henderson et al. | |

OTHER PUBLICATIONS

Aburahma, A.F., et al., "Iliofemoral deep vein thrombosis: Conventional therapy versus lysis and percutaneous transluminal angioplasty and stenting,"Ann Surg 233: 752-60, (2001).
Comerota, A.J., et al., "Catheter-directed thrombolysis for iliofemoral deep venous thrombosis improves health-related quality of life," J Vasc Surg 32: 130-7, (2000).
Delis, K.T., et al., "Successful iliac vein and inferior vena cava stenting ameliorates venous claudication and improves venous outflow, calf muscle pump function, and clinical status in post-thrombotic syndrome," Ann Surg 245: 130-9, (2007).
Elsharawy, M., et al., "Early results of thrombolysis vs anticoagulation in iliofemoral venous thrombosis. A randomised clinical trial," Eur J Vasc Endovasc Surg 24: 209-14, (2002).

(Continued)

*Primary Examiner* — Jonathan W Miles
(74) *Attorney, Agent, or Firm* — James W. Hill; McDermott Will & Emery LLP

(57) ABSTRACT

A fenestrated endograft having an expandable stent frame and a lumen is described herein. The stent frame has a proximal end portion, a distal end portion, and a central portion. The central portion may include a fabric that has an aperture partially surrounded by part of the expandable stent frame. The lumen extends through the proximal end portion, the central portion, and the distal end portion. The stent frame is radially expandable from a collapsed configuration to an expanded configuration. The central portion is coupled to a fabric, which extends about a perimeter of the central portion. The fabric has an aperture with a cross-sectional dimension that is substantially equal to a cross-sectional dimension of an outer cross-sectional dimension of the distal end portion. The central portion has a curved elongate member, which includes a curved segment extending around at least one-fourth of a perimeter of the aperture.

21 Claims, 22 Drawing Sheets

(56) References Cited

OTHER PUBLICATIONS

Kahn, S.R., "Frequency and determinants of the postthrombotic syndrome after venous thromboembolism," Curr Opin Pulm Med 12: 299-303, (2006).

Kahn, S.R., et al., "Determinants of health-related quality of life during the 2 years following deep vein thrombosis," J Thromb Haemost 6: 1105-12, (2008).

Labropoulos, N., et al., "Criteria for defining significant central vein stenosis with duplex ultrasound," J Vasc Surg 46: 101-107, (2007).

May, R., et al., [a vascular spur in the vena iliaca communis sinistra as a cause of predominantly left-sided thrombosis of the pelvic veins] Z Kreislaufforsch 45: 912-22 (1956).

Mewissen, M.W., et al., "Catheter-directed thrombolysis for lower extremity deep venous thrombosis: Report of a national multicenter registry," Radiology 211: 39-49, (1999).

Neglen, P., et al., "Angioplasty and stenting of the obstructed iliac vein," Hawaii Med J 59:276-8 (2000).

Neglen, P., et al., Bilateral stenting at the iliocaval confluence, J Vasc Surg 51: 1457-66 (2010).

Partsch, H., "Immediate ambulation and leg compression in the treatment of deep vein thrombosis," Dis Mon 51: 135-40, (2005).

Prandoni, P., "Long-term clinical course of proximal deep venous thrombosis and detection of recurrent thrombosis," Semin Thromb Hemost 27: 9-13 (2001).

Prandoni, P., et al., "Below-knee elastic compression stockings to prevent the post-thrombotic syndrome: A randomized, controlled trial," Ann Intern Med 141: 249-56, (2004).

Raju, S., et al., "Obstructive lesions of the inferior vena cava: Clinical features and endovenous treatment," J Vasc Surg 44: 820-7, (2006).

Vedantham, S., "Catheter-directed thrombolysis for deep vein thrombosis," Curr Opin Hematol 17: 464-468 (2010).

Vedantham, s., et al., "Development of a research agenda for endovascular treatment of venous thromboembolism: Proceedings from a multidisciplinary consensus panel," J Vasc Interv Radiol 16: 1567-73, (2005).

Vedantham, S., et al., "Quality improvement guidelines for the treatment of lower extremity deep vein thrombosis with use of endovascular thrombus removal," J Vasc Interv Radiol 17: 435-48, (2006).

Vedantham, S., et al., "Reporting standards for endovascular treatment of lower extremity deep vein thrombosis," J Vasc Interv Radiol 17: 417-34, (2006).

\* cited by examiner

FENESTRATED ENDOGRAFT

RELATED APPLICATIONS

The current application claims the benefit of priority from the provisional U.S. application No. 61/442,633, which is incorporated by its entirety hereinwith.

BACKGROUND

Deep venous thrombosis (DVT) is the most common cause of venous outflow obstruction. Venous outflow obstruction may be either acute or chronic. Patients with acute DVT usually present with sudden onset of unilateral leg swelling. This is often painful, associated with cyanosis of the extremity, and often after prolonged immobilization or sedentary activity. Chronic venous outflow obstruction usually occurs months to years after an initial DVT. In symptomatic patients, the body's own recanalization of thrombosed veins is incomplete, and the collateral circulation is inadequate. The proximal obstruction results in distal venous hypertension, lower extremity swelling, and pain worsened after ambulation. Although venous outflow obstruction of the lower extremity may involve the entire venous system, some endovascular techniques focus treatment on thrombosis of the largest veins, namely, the inferior vena cava (IVC), common iliac vein, and external iliac veins.

Catheter-directed thrombolysis and percutaneous mechanical thrombectomy (PMT) can be important therapies in patients with acute DVT, largely replacing venous bypass surgery. Initial clinical and technical success can be achieved in most patients with acute DVT. Early thrombus removal results in relief of lower extremity venous hypertension and improved long-term patency of the venous system.

SUMMARY

Central venous obstruction of the upper extremities is a challenging, yet increasing problem often associated with the use of chronic indwelling catheters for hemodialysis. Stenosis of the innominate vein or superior vena cava are becoming increasingly commonplace. These patients will often have failure of their upper extremity hemodialysis graft or arteriovenous fistula due to this venous outflow obstruction. Endovascular intervention with percutaneous balloon angioplasty and/or stent placement has emerged as first line treatment. Not unlike the lower extremities, there is no consensus on what the best stent configuration is to maintain the patency of the innominate vein or superior vena cava. The exact same stent configurations listed above are attempted in the chest with similar limitations and results.

There is a need for a simpler and more effective stent system suitable for use in venous confluences. The following fenestrated endograft provides a simple installation that provides a reliable treatment of stenosis of venous confluences as well as other applications.

A fenestrated venous stent graft system is described herein. In some embodiments, the system comprises an expandable stent frame and a lumen. The stent frame has a proximal end portion, a distal end portion, and a central portion between the proximal and distal end portions. The lumen may extend through the proximal portion, central portion, and distal end portion. The stent frame may be radially expandable from a collapsed configuration to an expanded configuration. The central portion may be coupled to a fabric that extends along a perimeter of the central portion and comprises an aperture having a cross-sectional dimension that is substantially equal to a cross-sectional dimension of an outer cross-sectional dimension of the distal portion. The central portion may comprise a curved, elongate member having a curved segment that extends around at least one-fourth of a perimeter of the aperture. The segment may have a radius of curvature that is less than 10 percent longer than a radius of curvature of the one-fourth of the perimeter of the aperture. The elongate member may provide a bias force that tends to resist collapse of the aperture when the stent frame is in the expanded configuration. The first and second portions of the elongate member may be adjacent to opposite ends of the segment, respectively and each has a curvature with a different sign than the curvature of the segment.

In some embodiments, the elongate member may comprise a wire. The wire may comprise Nitinol. At least one of the first and second portions of the elongate member may have a curvature that is opposite the sign of the curvature of the segment. The stent graft system may further comprise a second stent graft with a portion that is configured to extend through the aperture. The second stent graft may comprise a second aperture that is configured to be aligned with the lumen at the central portion when the second stent graft is extended through the aperture. The radius of curvature of the segment may be less than 5 percent longer than the radius of curvature of the one-fourth of the perimeter of the aperture. The radius of curvature of the segment may also be between about 5 percent and 10 percent longer than the radius of curvature of the one-fourth of the perimeter of the aperture. In some embodiments, at least one of the first and second portions of the elongate member may have a curvature that is opposite the sign of the curvature of the segment. The central portion of the expandable stent frame may comprise a sinusoidal shape that defines at least a portion of the central portion perimeter. The aperture may comprise an oval shape or a shape defined by a circle project onto a cylinder along a line that passes through a central axis of the cylinder and at an angle relative to an axis of the cylinder. The expandable stent frame may have a diameter, when in the expanded configuration, of between about 5 mm to about 30 mm. In some embodiments, the diameter of the expandable stent frame, when in the expanded configuration, may be of between about 12 mm to about 24 mm. The diameter, when in the collapsed configuration, may be of between about 2 mm to about 5 mm. The diameter, when in the collapsed configuration, may be of between about 3 mm to about 4 mm in some embodiments.

A method of implanting a stent graft system in a venous confluence is provided. A first expandable stent frame is advanced into a first vessel that drains into a venous confluence. The first expandable stent may be radially expandable from a collapsed configuration to an expanded configuration. The first frame has a proximal end portion, a distal end portion, and a central portion between the proximal and distal end portions. The expandable stent has a lumen extending through the proximal portion, central portion, and distal end portion. The central portion may be coupled to a fabric that extends along a perimeter of the central portion and comprises an aperture having a cross-sectional dimension that is substantially equal to a cross-sectional dimension of an outer cross-sectional dimension of the distal portion. The central portion may comprise a curved, elongate member having a curved segment that extends around at least one-fourth of a perimeter of the aperture, and the segment may have a radius of curvature that is less than 10 percent longer than a radius of curvature of the one-fourth of the perimeter of the aperture. The elongate member may provide a bias force that tends to resist collapse of the aperture when the stent frame is in the expanded configuration. In some embodiment, the first and second portions of the elongate member are adjacent to opposite ends of the segment, respectively, and each may have a curvature with a different sign than the curvature of the segment. The first stent frame is expanded at the venous confluence such that the one of the proximal end portion and the distal end portion resides within the first vessel and the other of the proximal end portion and the distal end portion resides at the confluence, and such that the aperture opens to a second vessel that drains into the confluence.

In some embodiments, a second stent graft may be advanced and expanded into the confluence such that one of a proximal end portion and a distal end portion of the second stent graft is positioned and extends within the one of the proximal end portion and the distal end portion of the first stent graft, and the other of the proximal end portion and the distal end portion of the second stent graft may extend through the aperture of the first stent graft and into the second vessel. The second stent graft may be positioned such that an aperture in a central portion of the second stent graft is aligned with the lumen of the first stent graft, to maintain fluid communication through the first stent graft. The patency of the aperture of the first stent graft may be maintained by expanding the second stent graft within the aperture.

In some embodiments, a fenestrated venous stent graft system is provided. The system comprises a first stent frame and a fabric. The first stent frame may include at least one curved segment extending about a center axis thereof. The curved segment may be configured with a plurality of repetitive curves having an amplitude A along a direction of the center axis and a period S along a perimeter of the first stent frame. The fabric may extend about the center axis and the perimeter of the first stent frame. The fabric has an aperture with an origin O' relative to the center axis, for example, the distance to the center axis, and a maximum diameter D determined based on a radius R of the perimeter of the first stent frame and the period S of the repetitive curves of the curved segment. In some embodiments, the origin O' and the maximum diameter D are determined by:

$$O' = R \cos(\pi/S)$$

$$D = 2R \sin(\pi/S)$$

The first stent frame may comprise a proximal end portion, a central portion and a distal end portion, and the curved segment extends only in the central portion. The fabric is coupled to the curved segment in a manner that forces the aperture open when the first stent frame is fully expanded. For example, the fabric may be coupled to the curved segment at three or more joints along a perimeter of the aperture. The curved segment may extend along at least ¼ of the perimeter of the aperture. The system may further comprise a second stent frame extending through the aperture towards the distal or proximal end portion of the first stent frame. The second stent frame may be expandable towards the first stent frame. The system may further comprise an indication such as a C mark attached on the curved segment or the fabric in a proximity of the aperture. The indication may be made of metal such as gold or other radiation opaque material.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
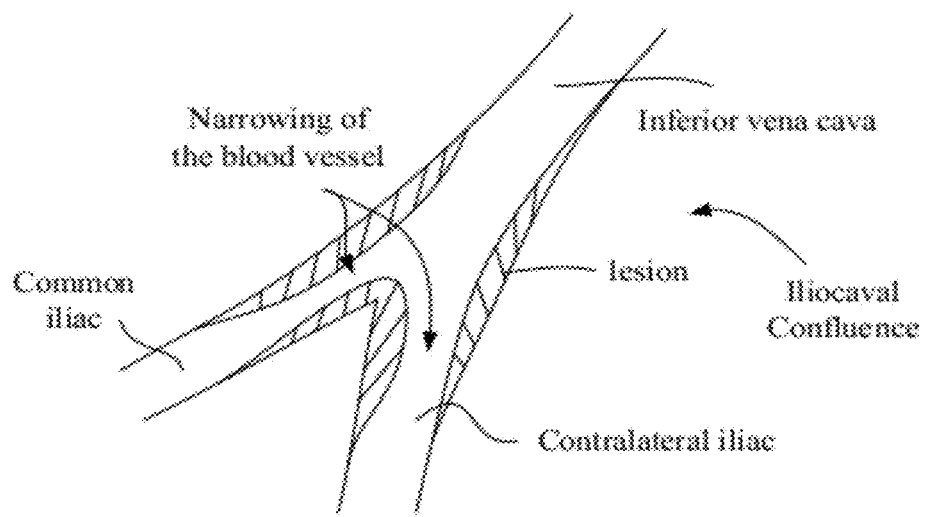
FIG. 1 illustrates the medical condition of stenosis of the iliocaval confluence.
Figure 2:
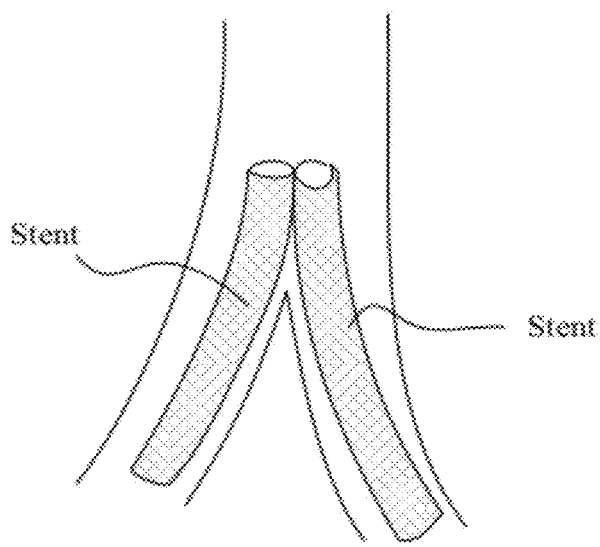
FIGS. 2 to 4 illustrate various methods of stenting an iliocaval confluence.
Figure 3:
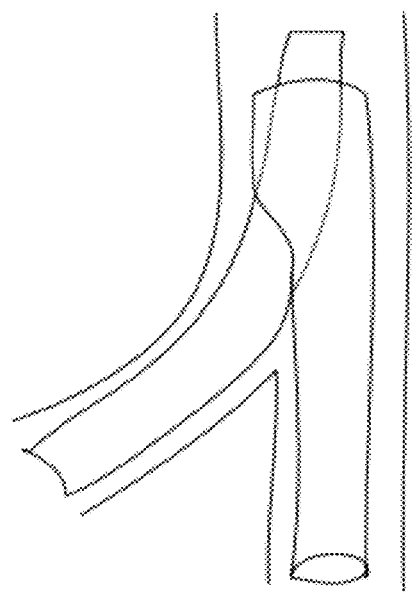
Figure 4:
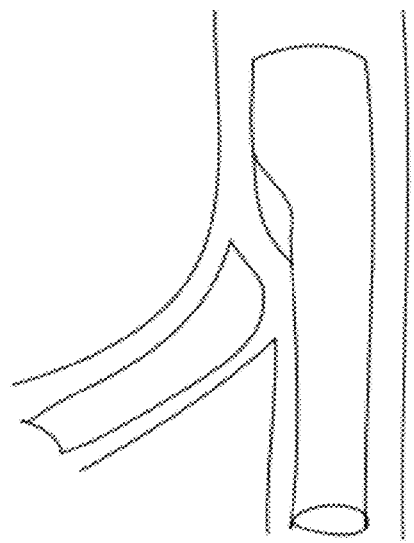

Stenosis, which is an abnormal narrowing, of a blood vessel may occur in the thrombosed vein. Clinical experience has shown that venous stenoses of the lower extremity rarely respond to angioplasty alone, and therefore, stenting is recommended. Stenting of confluences in the venous system, such as the confluence of the common iliac veins and vena cava, as illustrated in FIG. 1, is particularly challenging. Stents may be nitinol or stainless steel. Techniques that have been attempted for stenting of venous confluences include (i) placement of two stents side by side in a "double barrel" arrangement, as seen in FIG. 2, (ii) inverted Y-stenting of a stent through a fenestra (e.g., a window) created through the side braiding of a stent placed previously across the confluence, as shown in FIG. 3, and (iii) apposition of a stent as close as possible to a stent previously placed across the confluence, as illustrated in FIG. 4, leaving a small area unsupported between the stents.

Each of the above-mentioned techniques suffers from drawbacks. The double-barrel arrangement reduces the overall flow area due to the use of two smaller diameter stents, which is the same condition as the stenosis being treated. The Y-stenting of two currently available stents is a complex procedure and the effectiveness is dependent on the particular condition of the subject patient. The apposition technique requires a high reintervention rate owing to restenosis of the unsupported segment.

In the following detailed description, numerous specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology. Like components are labeled with identical element numbers for ease of understanding.

The terms "stentgraft," "endograft," "fenestrated stentgraft," "fenestrated endograft," and "fenestrated venous stentgraft" have been used herein to identify the same item and should be considered equivalent, including combinations and further variations of these terms. The term "stent" is considered to cover all forms of expandable elements that retain their shape after expansion and are suitable for use in the vessels of the human body, e.g., veins and arteries. The term "graft" is considered to cover all forms of artificial structures that replace or supplement natural elements of the body, e.g., tubular fabric structures.

FIG. 1 illustrates the medical condition of stenosis of the iliocaval confluence. FIGS. 2-4 illustrate current methods of stenting an iliocaval confluence. FIG. 2 illustrated a "double-barrel" placement of two stents side by side, one from each tributary vein with both stents extending into the common outflow vein. FIG. 3 is an "inverted-Y" stenting, being inverted when used in a lower body confluence, wherein a fenestra is created in the side braiding of a current stent while the stent is in place in one of tributary veins, then introducing a second stent through the fenestra from the other tributary vein. In certain embodiments, a second fenestra (not shown) is created in the second stent within the first stent after the second stent is in place. FIG. 4 illustrates a first stent placed across the confluence from one of the tributary veins into the larger outflow vein, with a second stent placed as close as possible to the first stent, leaving a small area unsupported gap between the stents.

Figure 5A:
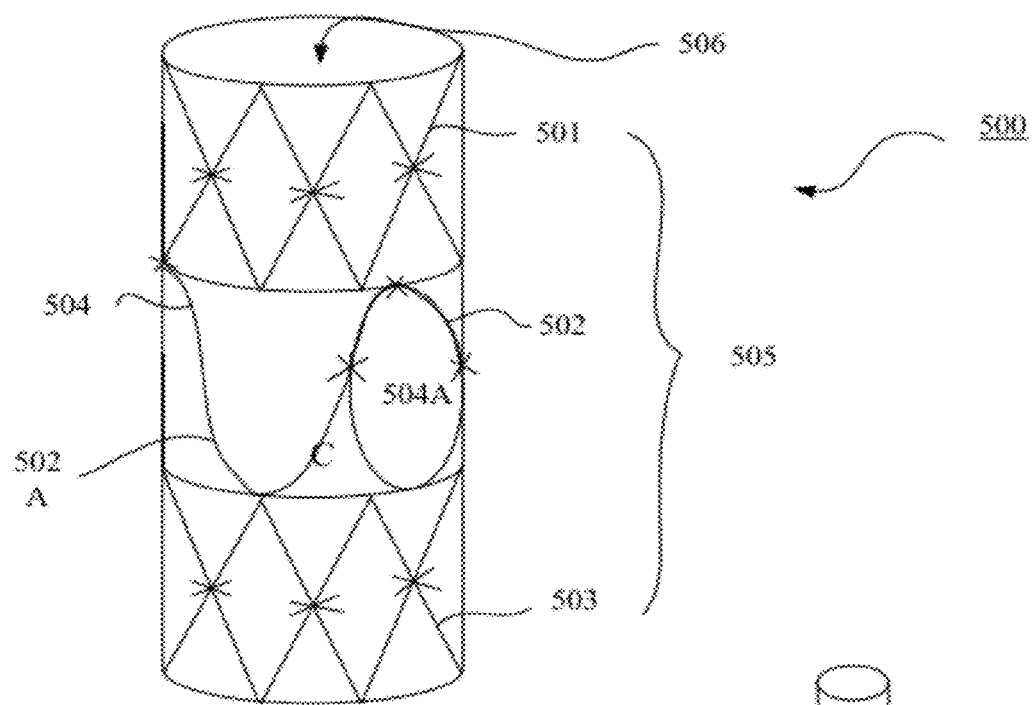
FIGS. 5A to 5B illustrate embodiments of a fenestrated endograft.
Figure 5B:
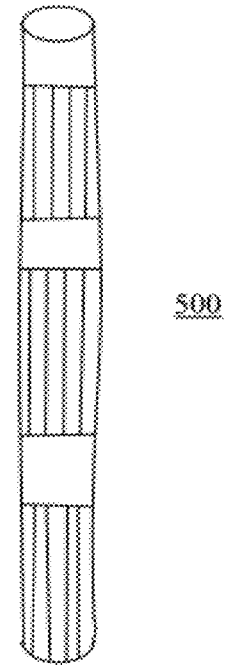

FIGS. 5A-5B illustrate one exemplary fenestrated endograft 500 according to certain embodiments of this disclosure. FIG. 5A illustrates the endograft 500 in an expanded configuration, such as after placement or deployment in a patient. In some embodiments, the endograft 500 comprises a stent frame 505 which may be formed of three stent members 501, 502, and 503. The stent frame can 505 may be made of expandable materials such as a metal wire. The stent frame may be made of Nitinol. The stent frame 505 may comprise other biocompatible materials that are expandable or that have shape-memory properties. The stent frame 505 may be expandable, for example, radially, from a collapsed configuration, or collapsible from an expanded configuration. In some embodiments, these three stent members 501, 502, and 502 may be arranged and sutured in series to form a proximal end portion 501, a central portion 502, and a distal end portion 503, respectively. As shown, the expanded stent frame 505 defines a tubular or cylindrical stent lumen 506 therein. The stent lumen 506 provides a fluid communication or fluid passageway throughout the proximal end portion 501, the central portion 502, and the end distal portion 503 of the stent frame 505. In some embodiments, the proximal and distal portions 501 and 503 may be of an open-cell stent design, while he central portion 502 may uniquely include at least one curved segment, for example, a series of sinusoidal waves, extending along a perimeter thereof or the lumen 506 defined by the stent frame 505.

The central portion 502 preferably includes a curved, elongate member 502A. This elongate member 502A can be integrally formed with the proximal end portion 501 and/or the distal end portion 503 of the stent frame 505. The elongate member 502A may otherwise be a separate member that is coupled to the proximal end portion 501 and/or the distal end portion 503 of the stent frame 505. In some embodiments, the elongate member 502A is a separate member that is not directly coupled to the proximal end portion 501 and/or the distal end portion 503 of the stent frame 505. Various flexibilities are available for the central portion 502 by adjusting the elongate member 502A in size, shape, connectivity to portions of the stent frame 505, etc. In some embodiments, in which greater flexibility is desired, the elongate member 502A extending in the central portion 502 is not directly connected to the proximal end portion 501 or distal end portion 502 of the stent frame 505.

The stent frame 505, or at least the central portion 502 of the stent frame 505, is coupled to a fabric 504 such as a thin-walled Dacron graft with an aperture, an opening, or a fenestration 504A therein. The fabric 504 may be a nonporous material, such as polymer sheets and films. In the example as shown in FIG. 5A, the fenestration 504A is aligned within the central portion 502. The fenestration 504A may be configured to fit a body lumen of the patient. For example, the fenestration 504A may have a cross-sectional dimension substantially equal to a cross-sectional dimension of an outer cross-sectional dimension of the distal portion 503. The similar sizing of the aperture 504A and the cross-section dimension of an outer cross-section dimension of the distal portion 503 facilitates deployment and functionality of the stent graft system 500 when used with a second stent graft 610 as illustrated in FIG. 6F. In some embodiments, the aperture 504A comprises an oval shape, and in some embodiments, the aperture 504A comprises at least a portion having an oval shape. The aperture 504A may comprise a shape that is defined by a circle projected onto a cylinder wall along a projection line that passes through a central axis of the cylinder and at an angle relative to a central axis of the cylinder. The curved segment 502A of the central portion 502 extends along at least a part of the perimeter of the fenestration 504A. The curved segment 502A may be in contact or tied with the perimeter of fenestration 504A at three points so as to extend or edge about at least ¼ of the perimeter of the fenestration 504A; and thereby provides a bias or force to keep the fenestration 504A open. The curved segment 502A may have a radius of curvature that is less than 10% than a radius of curvature of the ¼ of the perimeter of the fenestration 504A. The radius of the curvature of the curved segment 502A may be as small as less than about 5% than the radius of curvature of the ¼ of the perimeter of the fenestration 504A. The endograft 500 may further comprise a metal or radio-opaque mark, e.g., an asymmetric symbol or character such as a letter "C" formed from metal such as gold sewn or adhered onto the fabric 504 adjacent to the fenestration 504A. Thereby, radiation such as x-ray imaging can be used during the insertion procedure to facilitate orienting the fenestration 504A in the desired direction and location.

FIG. 5B shows the endograft 500 of FIG. 5A in a compressed configuration such that it can be inserted within a sheath for introduction through a blood lumen, vessel, or other channel in the human body. It is appreciated that, apart from the radial expansion, the stent frame 505 may also be configured to be expandable along various orientations or directions, for example, longitudinally or laterally. The configuration as shown in FIG. 5B allows the endograft 500 to be loaded into a hydrophilic sheath, for example, the sheath 600 as shown in FIG. 6A, with a tapered tip to facilitate insertion into a body lumen of a patient.

In certain embodiments, the stent frame 505 can, when fully expanded, come in diameters of about 5-30 mm. The fully expanded diameter of the stent frame 505 may be about 12-24 mm. The fenestration 504A can increase in size along with graft diameter in sizes about 14-24 mm. In other embodiments, the diameters are small and larger. In this embodiment, all of the component stents are 30 mm in length and the overall graft length would be standardized at 90 mm. In certain embodiments, the endograft 500 is fully expanded when the graft material is under tension around the entire circumference of the tubular graft. In the collapsed configuration, the stent frame 505 may have a diameter of about 2-4 mm, or between about 3-4 mm, for example. In some embodiments, the diameter of the stent frame 505, when in the collapsed configuration, is less than about 2 mm, and in some embodiments, the diameter of the stent frame, when in the collapsed configuration, is greater than about 5 mm.

FIGS. 6A-6F illustrate the method of utilizing a fenestrated endograft to stent an iliocaval confluence according to certain embodiments of this disclosure.

Figure 6A:
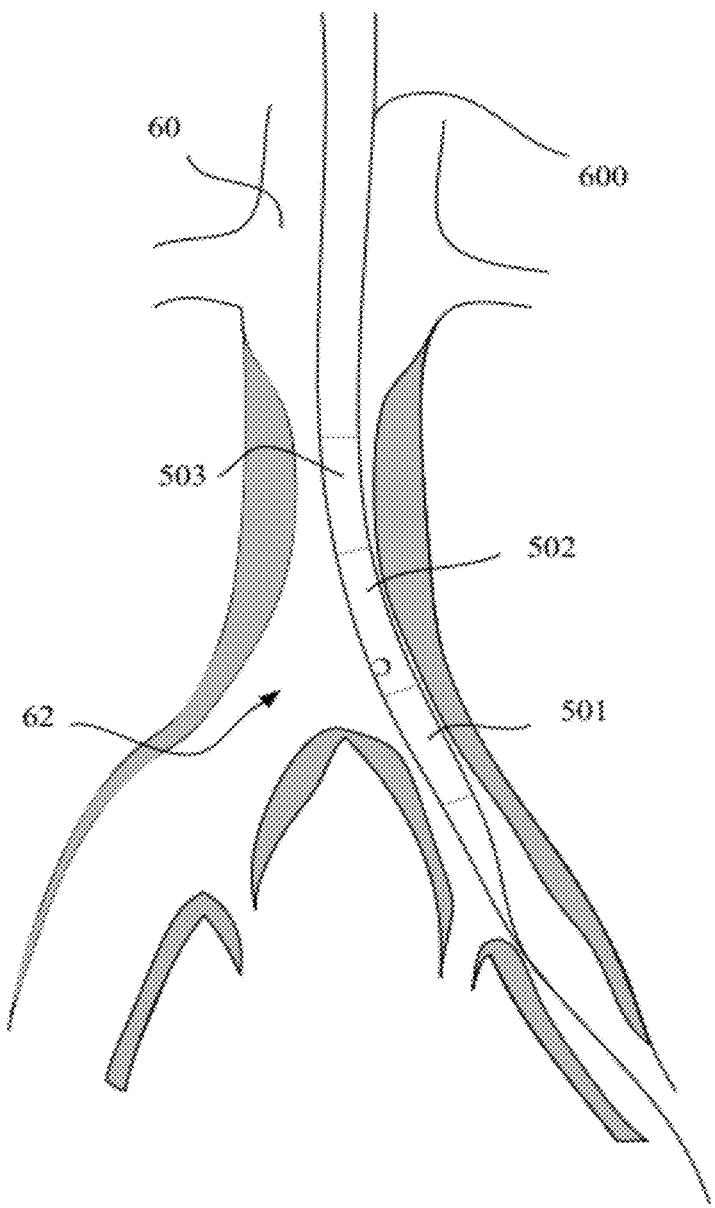
FIGS. 6A to 6F illustrate a method of utilizing a fenestrated endograft to stent an iliocaval confluence according to certain embodiments of this disclosure.

FIG. 6A illustrates an application of the venous graft with a fenestration or aperture similar to the endograft 500 as shown in FIG. 5, for example. After predilation of the venous occlusion or stenosis, such as with an angioplasty balloon, the stentgraft device 500 carried within a sheath 600 is delivered into position over a stiff guidewire 601. Before being deployed in the desire location, the stentgraft device 500 may be in the compressed configuration as shown in FIG. 5B. The metal, such as gold marker C attached next to the fenestration 504A may be radio opaque, such that a cannulation gate orientation may be indicated by the C marker to line up anterior/posterior and left/right toward contralateral venous lumen 60. In some embodiments, the expandable stent frame 505 has a diameter, when in the expanded configuration, of between about 5 mm to about 30 mm. In certain embodiments, the stent frame 505 has a diameter, when in the expanded configuration, of between about 12 mm to about 24 mm. In some embodiments, the diameter of the stent frame, when in the expanded configuration, is less than about 5 mm, and in some embodiments, the diameter of the stent frame 505, when in the collapsed configuration, is greater than about 30 mm.

Figure 6B:
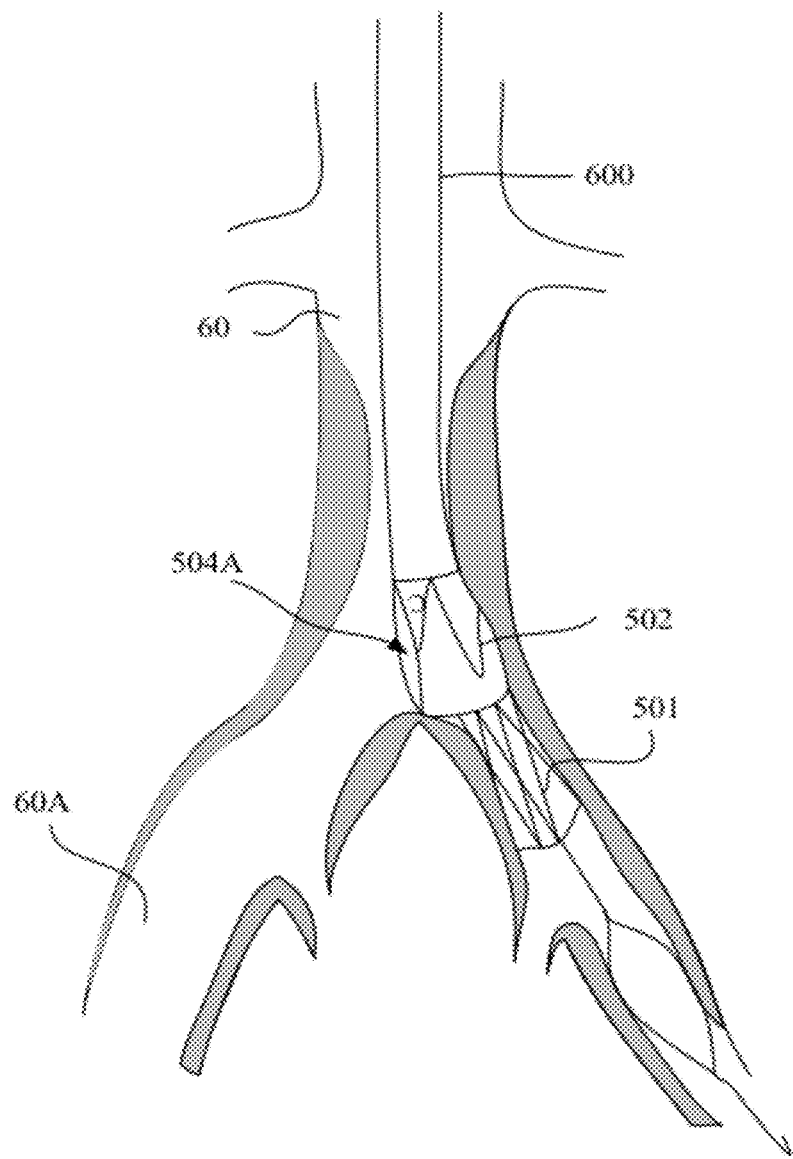
Figure 6C:
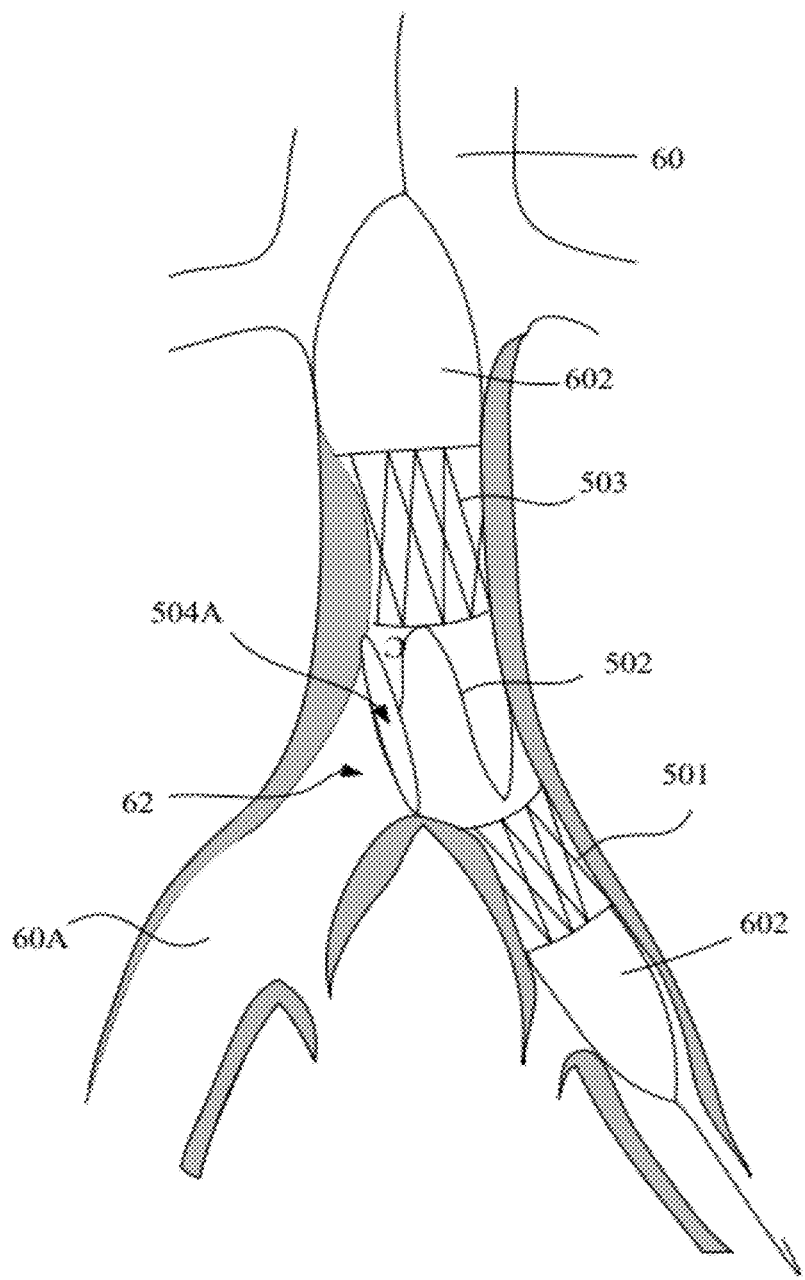

As shown in FIG. 6B, when the sheath 600 is positioned at the desired location in the venous lumen 60, the outer sheath 600 of delivery system is pulled back to allow the self-expanding stentgraft 500 to be deployed in a position adjacent to the contralateral common iliac vein orifice 62. As shown, the stent members 501 and 502 released from the sheath 600 start to expand against the walls of the venous lumen 60, followed by the self expansion of the stent member 503 as the sheath 600 is pulled further away as shown in FIG. 6C. When the sheath 600 is completely pulled away from the endograft device 500, an angioplasty balloon 602 with an appropriate size may be used to further dilate the endograft device 500. As shown in FIG. 6C, the fenestration 504A may be positioned across the contralateral common iliac vein orifice 62 to allow a contralateral stent, for example, the stent 610 as shown in FIG. 6E to be inserted from the contralateral venous lumen 60A into the endograft device 500.

Figure 6D:
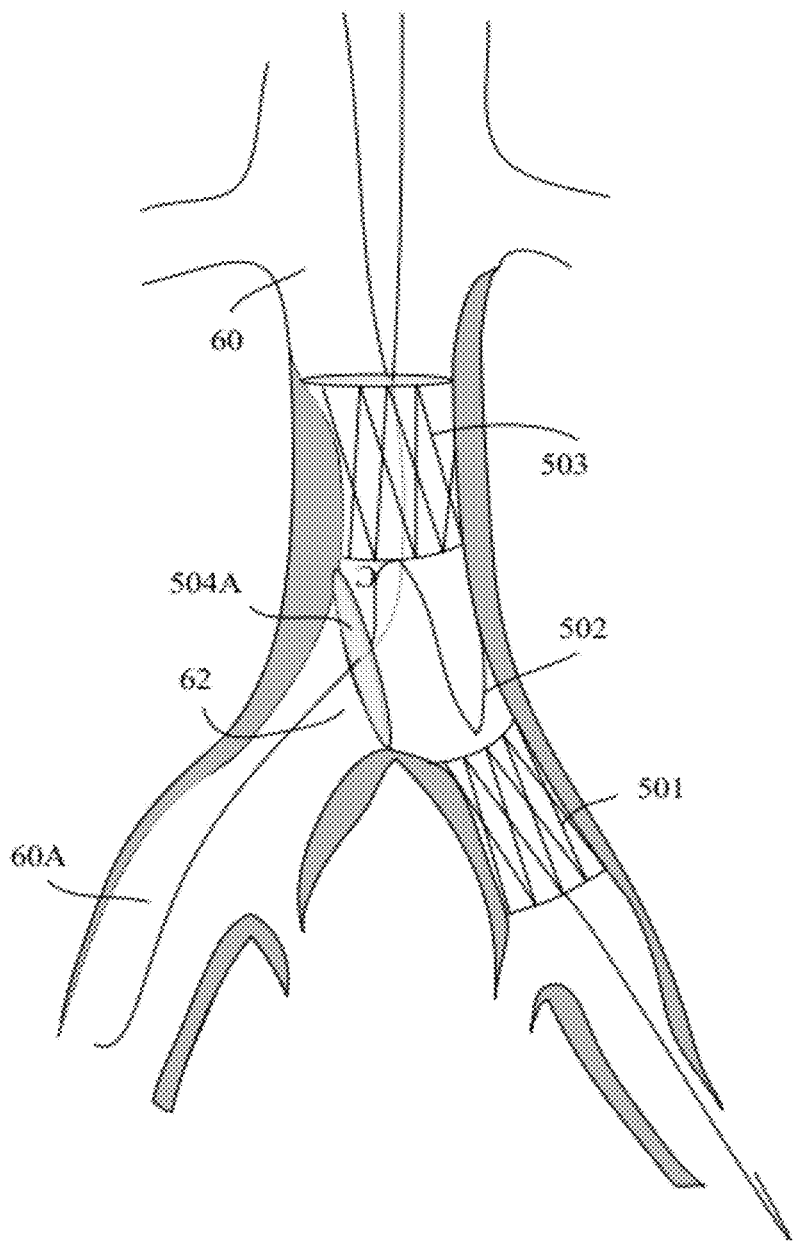

FIG. 6D illustrates the first stentgraft 500 in place after the angioplasty. As shown, the fenestration 504A is aligned with the contralateral common iliac vein orifice 62 to define a contralateral port.

Figure 6E:
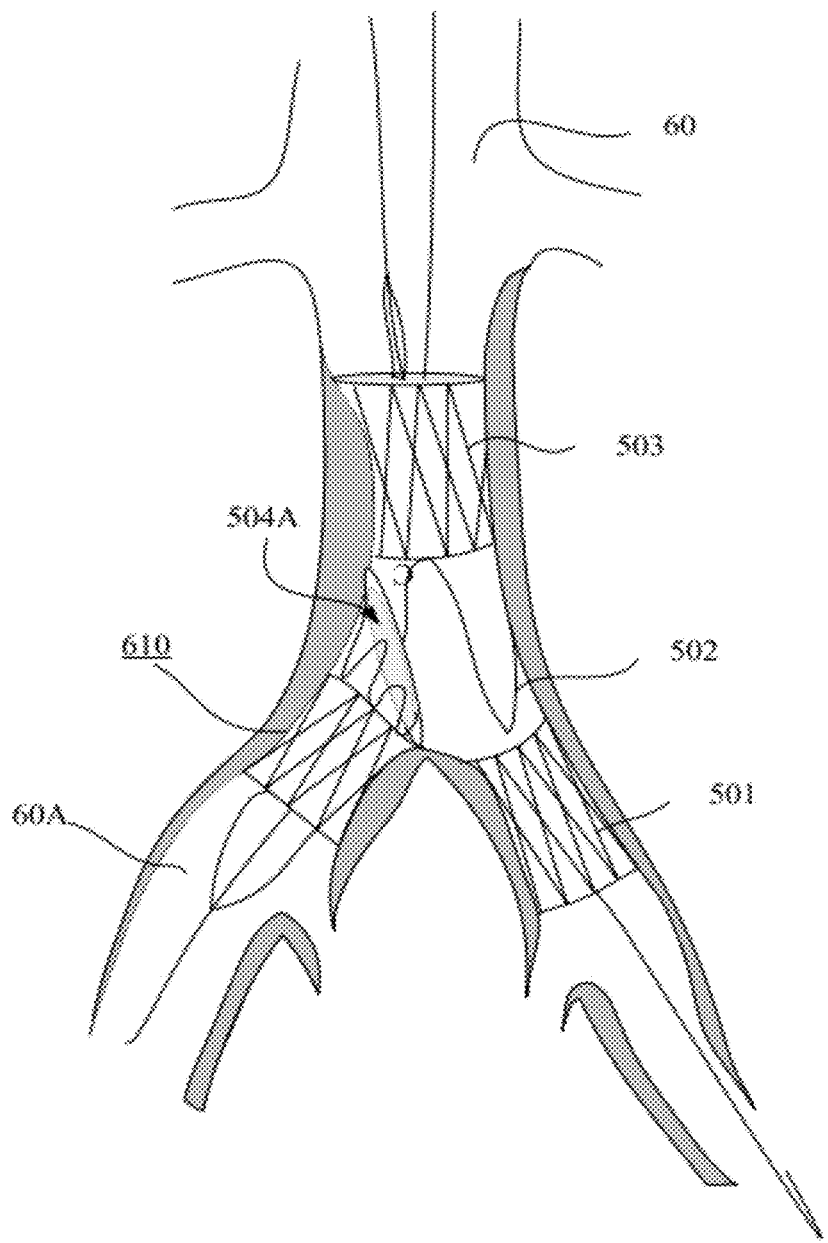
Figure 6F:
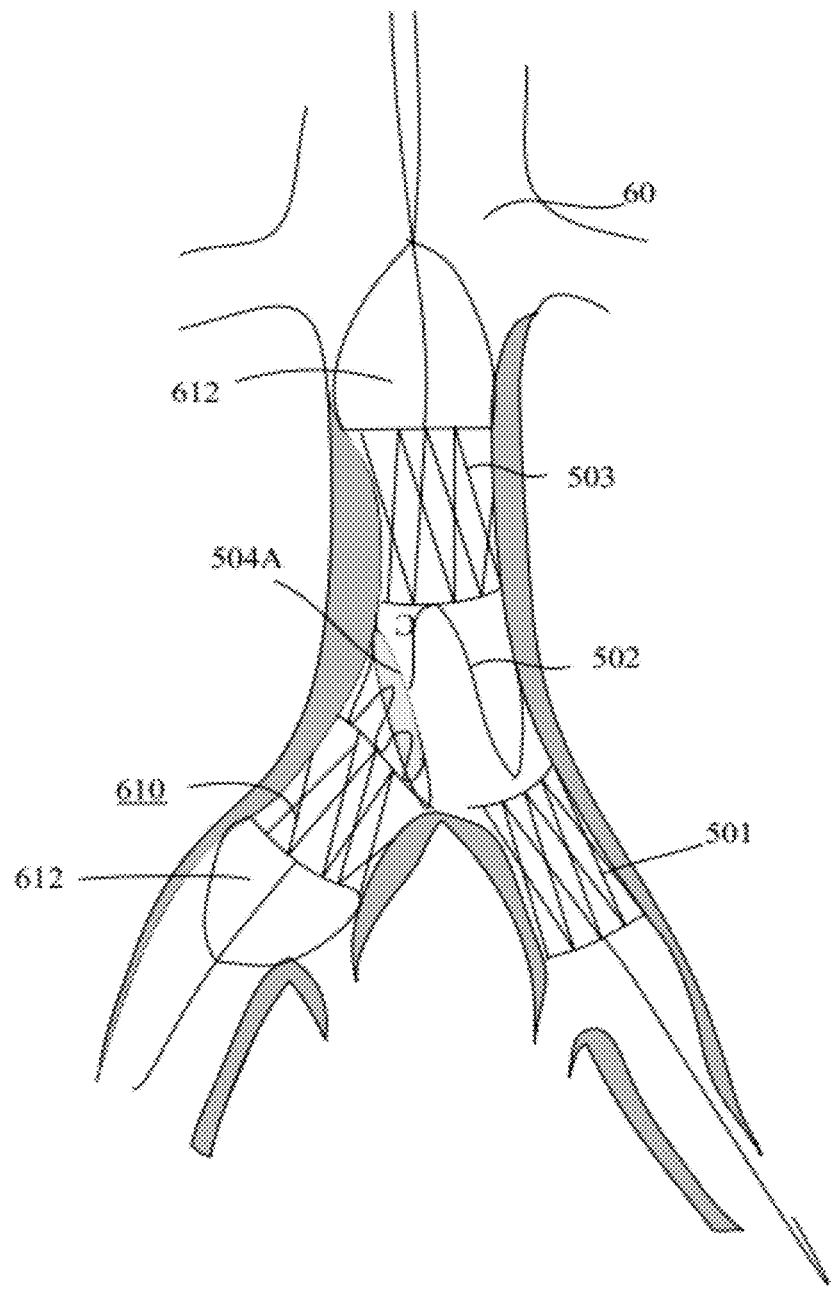

FIG. 6E depicts the second stentgraft 610 being inserted through the fenestration 504A of the first endograft 500 into the contralateral iliac after cannulation of the contralateral gate. In some embodiments, the second stentgraft 610 may be a fenestrated venous stentgraft with a structure similar to the first endograft 500. The second stentgraft 610 may be deployed in a similar manner for deploying the first endograft 500. After the second stentgraft 610 is deployed and extends through the venous lumen 60, as shown in FIG. 6F, an angioplasty balloon 612 is inserted through the second stentgraft 610 to further dilate the second stentgraft 610. Thereby, the second stentgraft 610 has a portion extending through at portions of the central portion 502 and the proximal end portion 501 of the endograft 500, and another portion extending along the contralateral venous lumen 60A. The portion extending through the portions of the endograft 500 may expand towards the expanded stent frame 505, while the portion extending through the contralateral venous lumen 60A may extend against the sidewall of the lumen 60A. Thereby, a fluid communication or passageway is established.

Figure 7:
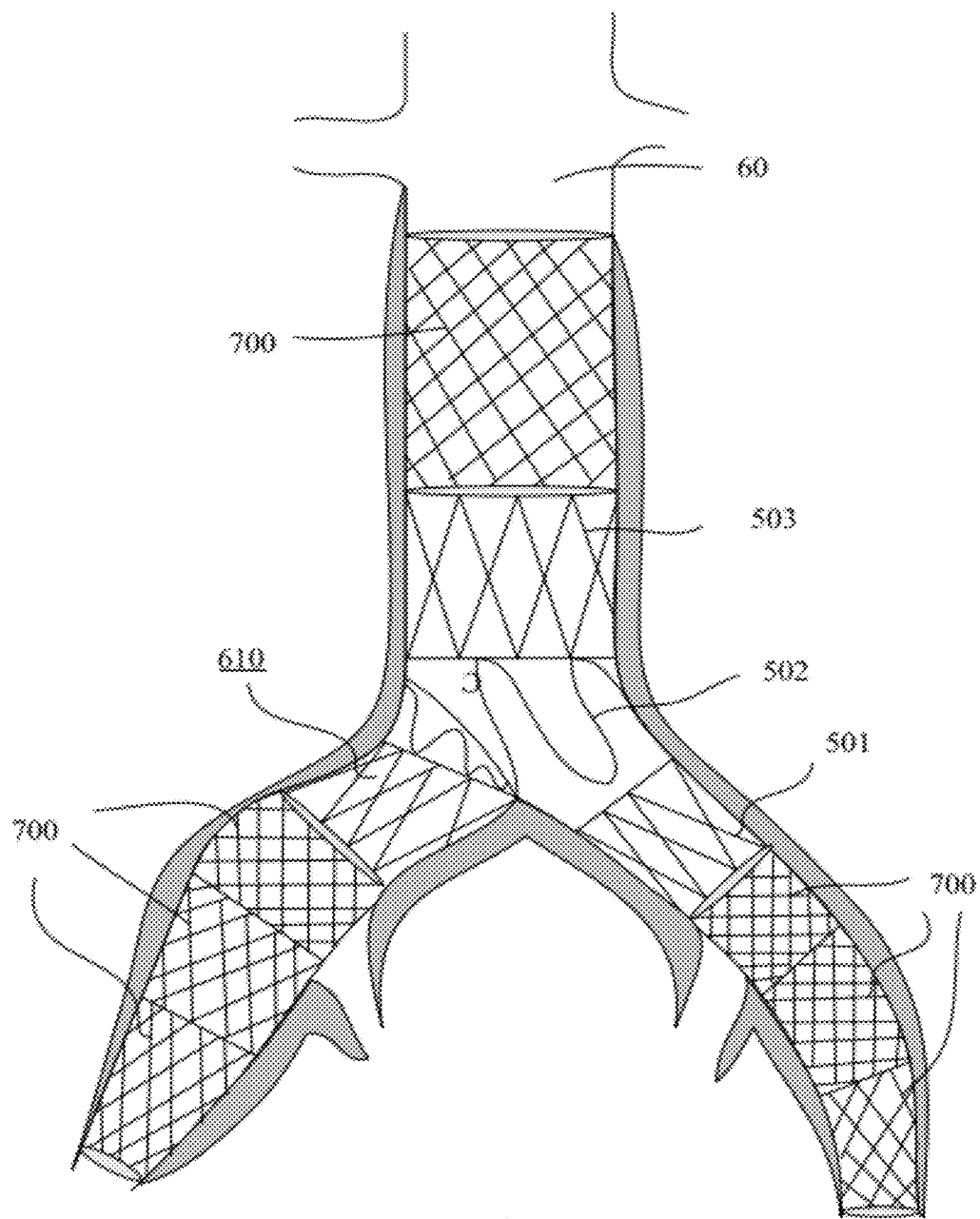
FIG. 7 illustrates the further placement of stents in the inflow and outflow veins according to certain embodiments of this disclosure.

As shown in FIG. 7, in some embodiments, once the first stentgraft 500 and the second stentgraft 610 are deployed and secured at the desired location, for example, the bifurcated venous lumens 60 and 60A, the iliac vein confluence is reconstructed. Additional stents 700 may further be installed in the inflow and/or outflow of the venous lumen 60 and/or 60A using standard techniques.

Figure 8:
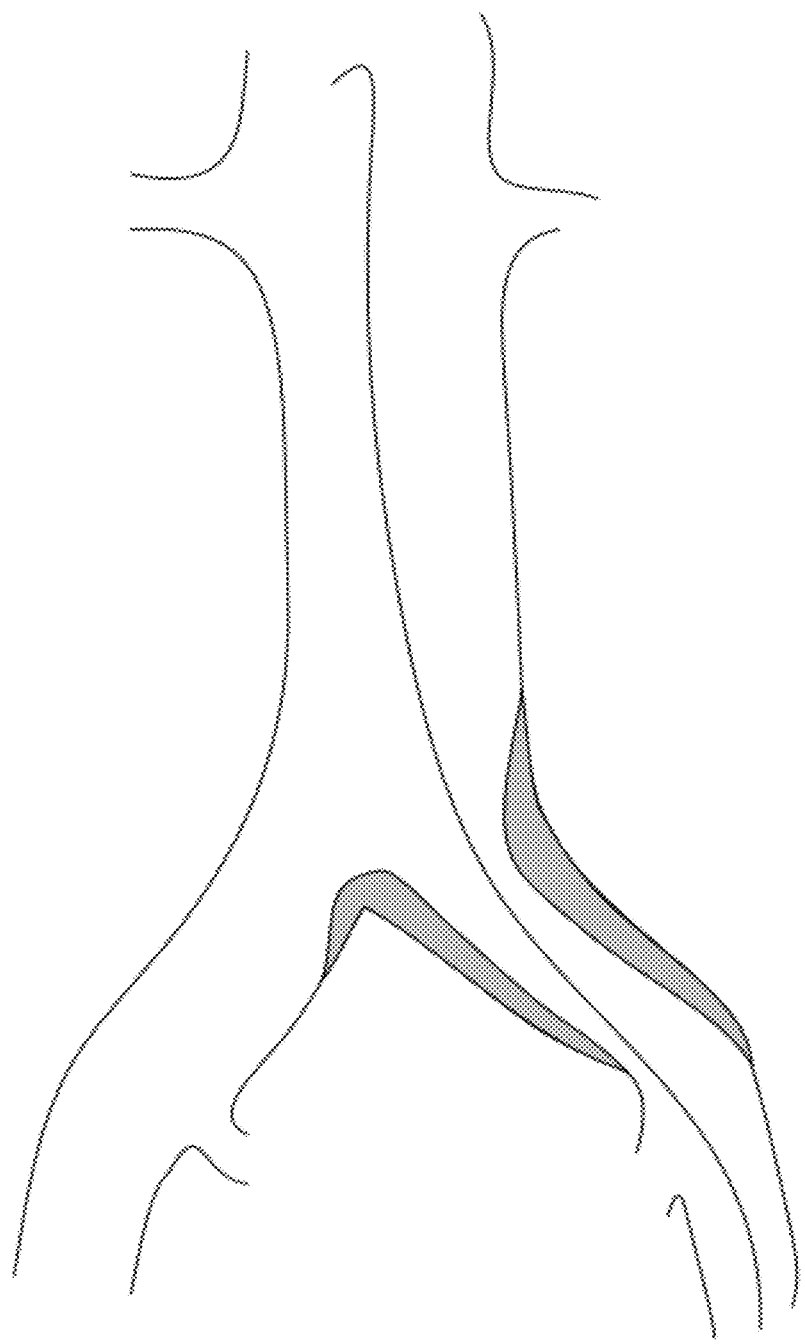
FIG. 8 illustrates an example of unilateral iliac venous obstruction.
Figure 9A:
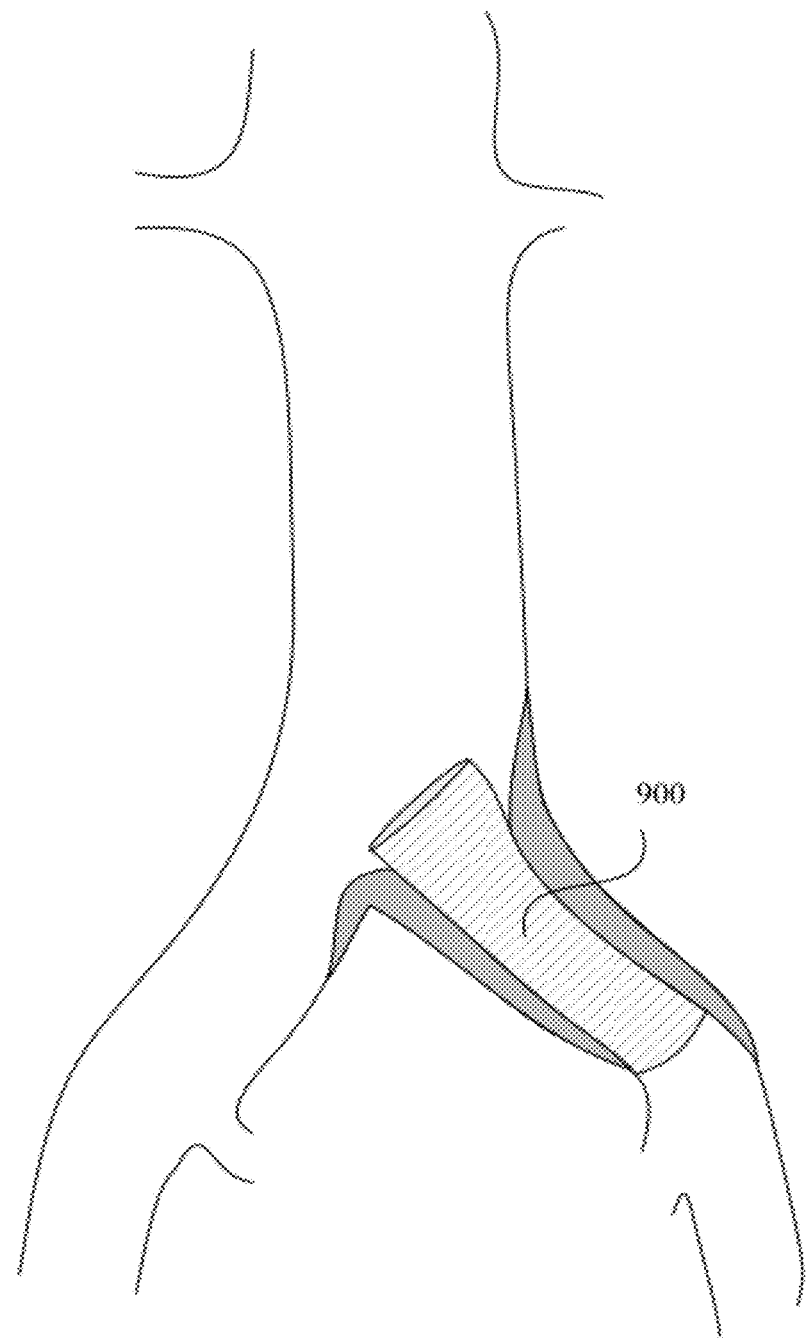
FIGS. 9A to 9B illustrate the current "hanging stent" method of treating unilateral iliocaval stenosis and a typical failure pattern.
Figure 9B:
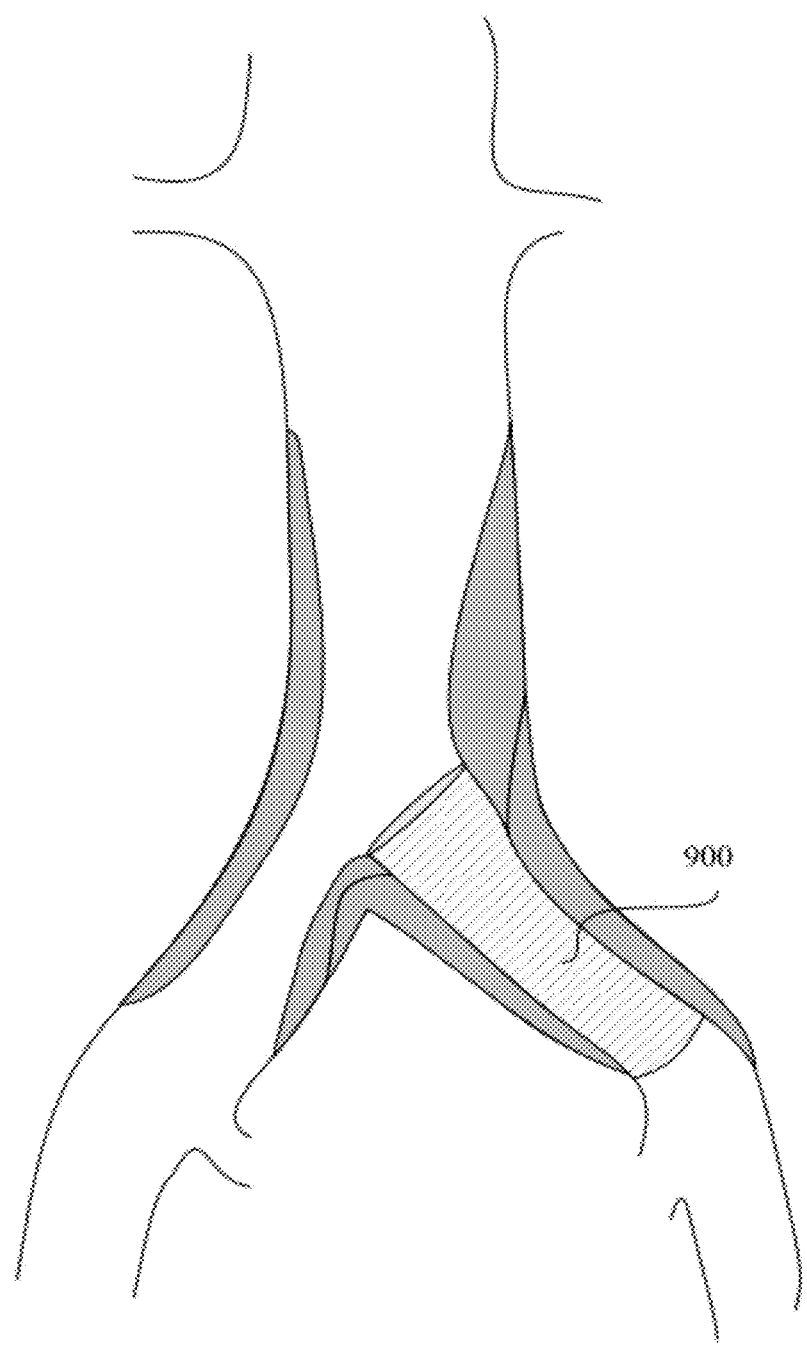

Cases of unilateral iliac venous obstruction are more common than bilateral cases and may not be associated with a thrombotic state. FIG. 8 shows an example of unilateral iliac venous obstruction. This nonthrombotic iliac vein stenosis may be treated with venoplasty and stenting techniques similar to those used in thrombotic cases. FIGS. 9A and 9B show an exemplary configuration, that is, a "hanging stent 900," operative to treat the unilateral iliac venous obstruction. As shown in FIG. 8A, the "hanging stent" configuration centers a single stent on the lesion but does not extend the stent into the vena cava. This theoretically uses the strongest part of the stent in the most difficult part of the lesion and spares the contralateral side. These stents are often undersized and associated with stent thrombosis involving both common iliac veins as seen in FIG. 9B.

Figure 10A:
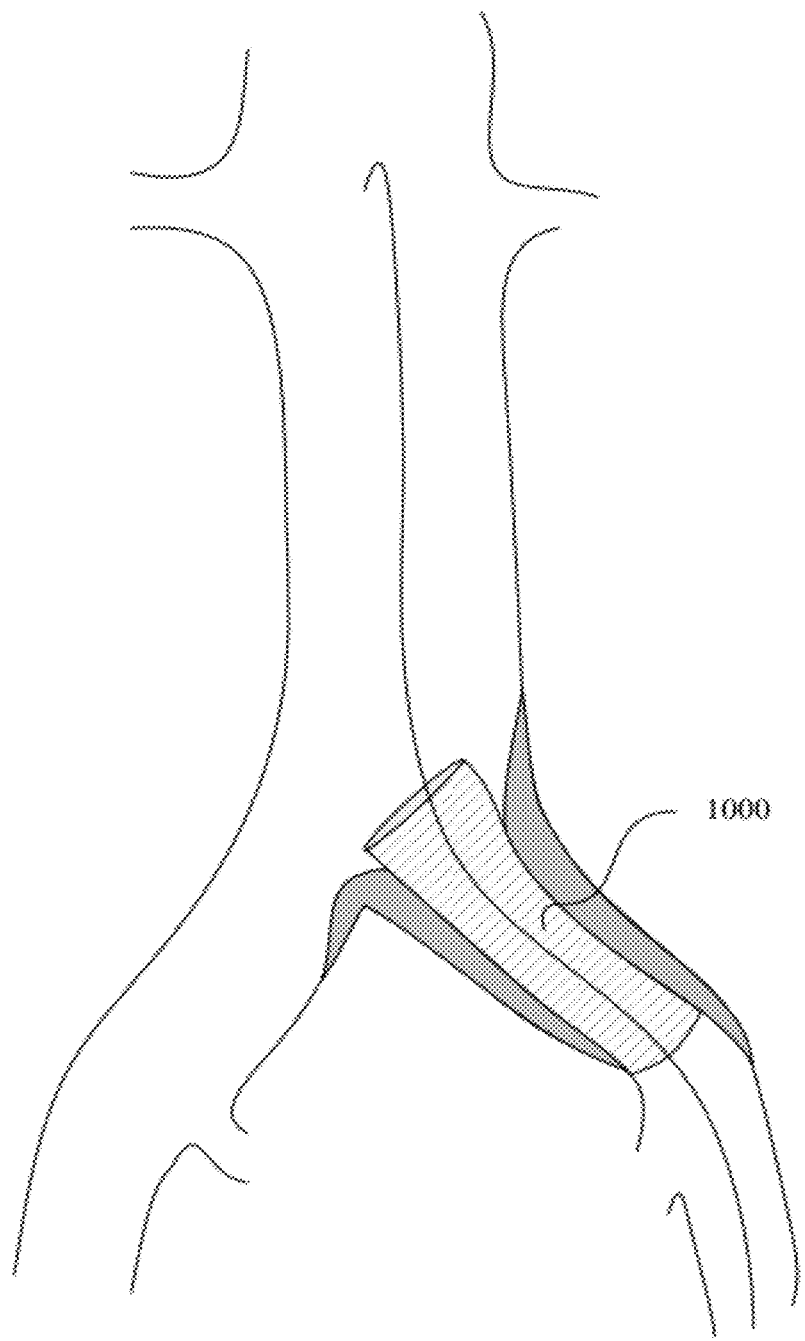
FIGS. 10A to 10B illustrate the current "understenting" method of treating unilateral iliocaval stenosis and a typical failure pattern.
Figure 10B:
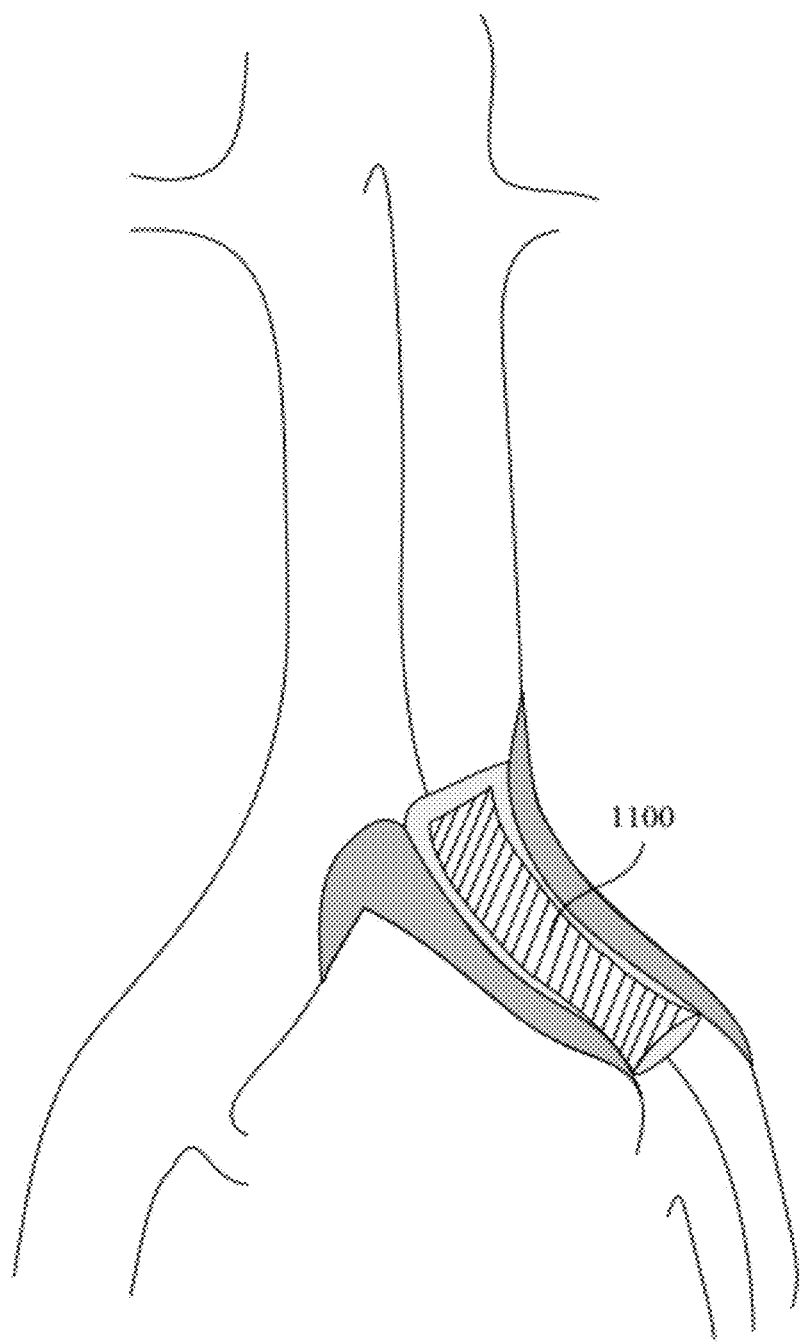

FIGS. 10A-10B illustrate an "understenting" method of treating unilateral iliocaval stenosis. "Understenting" the lesion is often performed as shown in FIG. 10A for fear of causing problems with the contralateral iliac vein. Unfortunately this technique may center the weakest portion of the stent 1000 in the worst part of the lesion. As a consequence, these stents can thrombose due to narrowing at this distal end as shown in FIG. 10B.

Figure 11A:
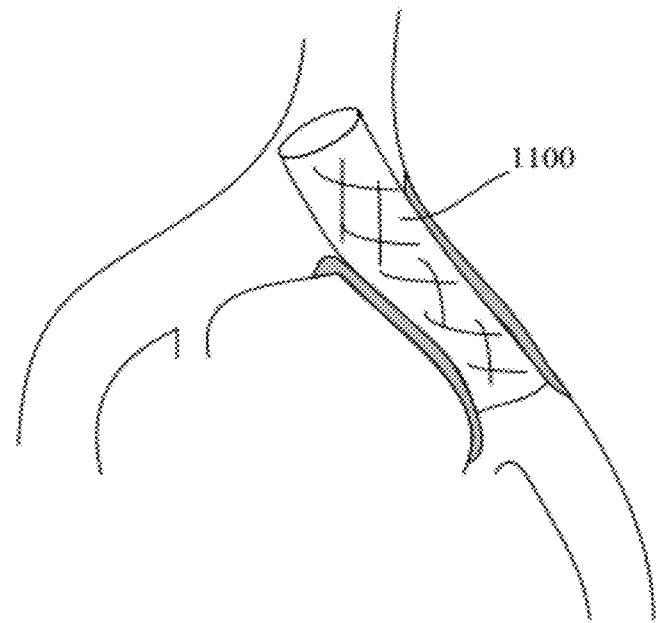
FIGS. 11A to 11B illustrate the current "extended stenting method" of treating unilateral iliocaval stenosis and a typical failure pattern.
Figure 11B:
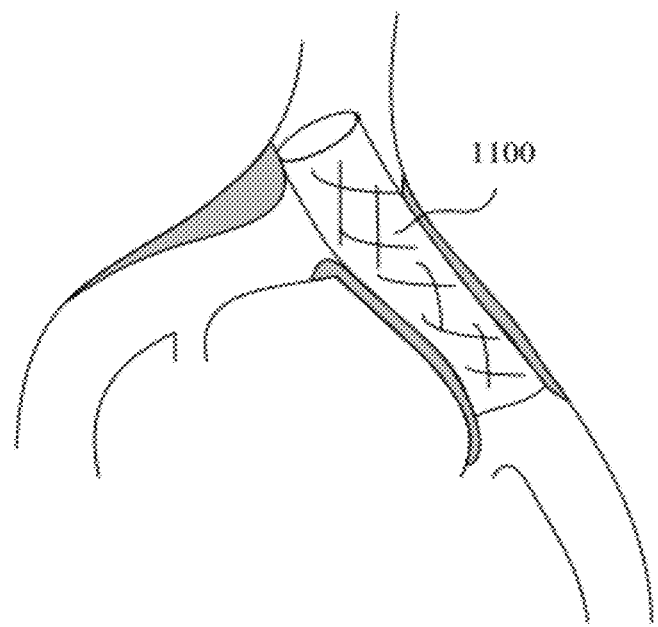

FIGS. 11A-11B illustrate an "extended stenting" method of treating unilateral iliocaval stenosis. Extending the stent 1100 into the vena cava is often used to treat unilateral iliac vein lesions. As shown in FIG. 10A, this stent configuration centers the stent 1100 on the lesion and allows for the use of larger stents to help the stent 1100 be adjacent to the wall of the vena cava. This technique, however, by definition places the stent 1100 across the orifice of the contralateral common iliac vein and can lead to contralateral iliac vein thrombosis, as shown in FIG. 10B.

Figure 12A:
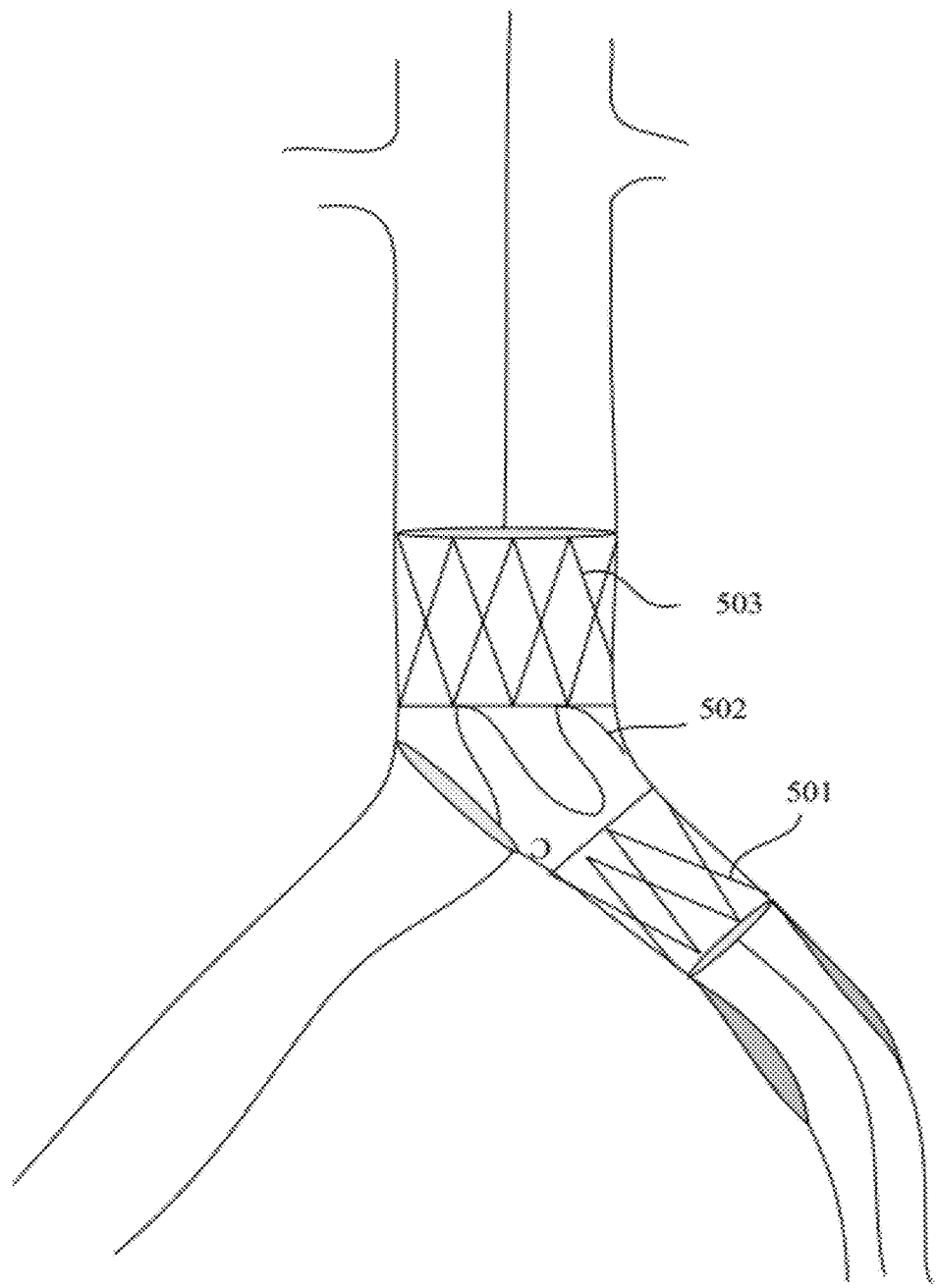
FIGS. 12A to 12B illustrates the use of a fenestrated endograft to treat stenosis at the confluence of the superior vena cava and the left and right brachiocephalic veins.
Figure 12B:
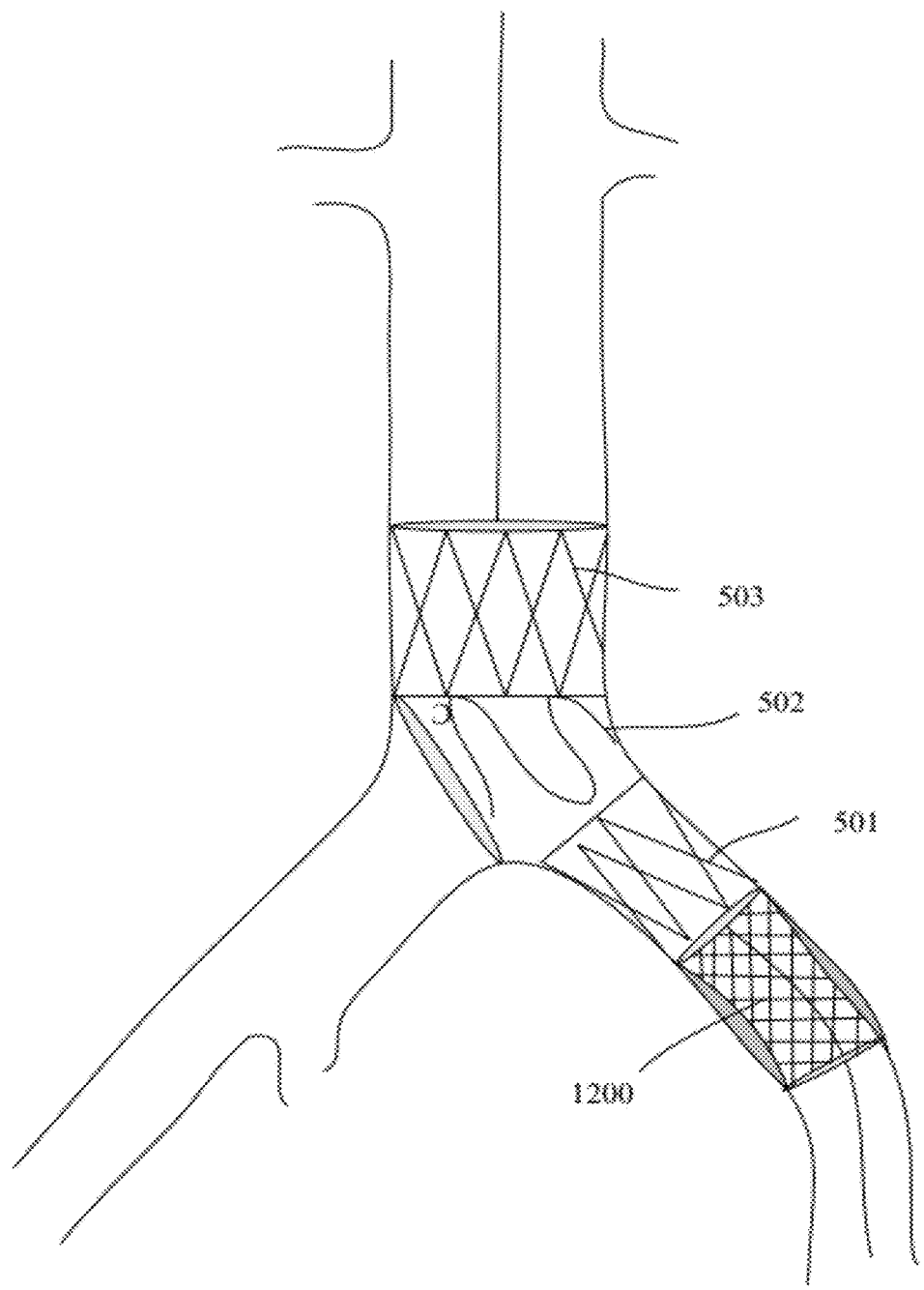

FIGS. 12A and 12B shows the application of the fenestrated endograft, for example, the stentgraft 500 as shown in FIG. 5, to the unilateral iliac venous obstruction. As shown in FIG. 12A, as the fenestration 504 of the fenestrated endograft 500 is aligned with the contralateral common iliac vein orifice 62, use of the fenestrated endograft 500 has the advantages of delivering the strongest portion of the stentgraft over the lesion while avoiding obstruction the contralateral iliac vein. This allows aggressive treatment of the lesion at the iliocaval junction and leads to a lower incidence of this complication. It would also allow extension of the conventional open cell stents to treat the remaining portion of the lesion.

FIG. 12B illustrates the placement of additional stents 1200 to cover the entire lesion according to certain embodiments of this disclosure. Once the stentgraft 500 is delivered, the interventionist can use typical stenting techniques to insure that the entire lesion is covered with the strongest portions of the stent maintaining the largest lumen possible. The fenestrated venous stentgraft 500 can be used in the less complex cases of nonthrombotic iliac vein stenosis. While it provides the advantages of delivering the strongest portion of the stentgraft over the lesion, the venous endograft 500 would not obstruct the contralateral iliac vein orifice and leads to a lower incidence of complication. It also allows extension of the conventional open-cell stents to treat the remaining portion of the lesion.

Figure 13:
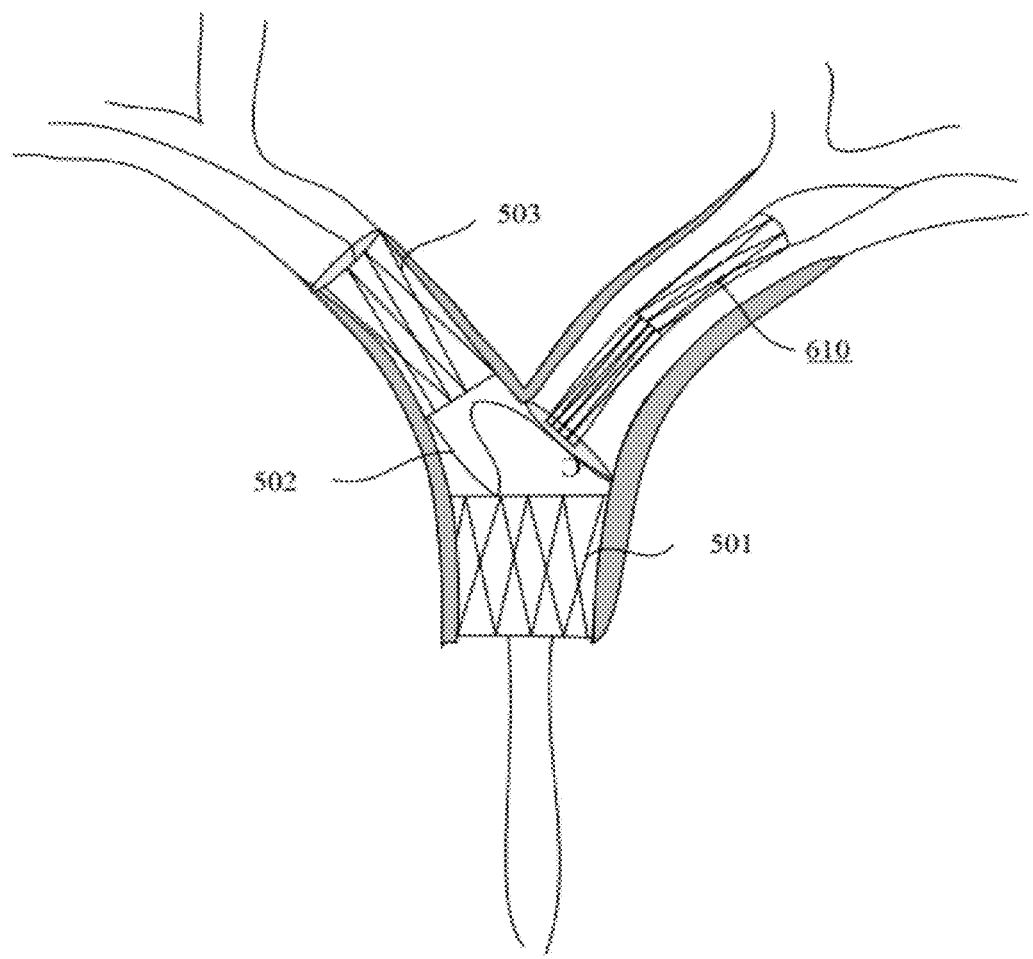
FIG. 13 illustrates the use of a fenestrated endograft to treat stenosis at the confluence of the superior vena cava and the left and right brachiocephalic veins.

Central venous obstruction of the upper extremities has been a challenging and increasing problem. This problem is often associated with the use of chronic indwelling catheters for hemodialysis. While thrombosis of the subclavian vein should have decreased due to the technique of using jugular venous insertion, stenosis of the innominate vein or superior vena cava are becoming increasingly commonplace. Patients with this problem often have the failure of the upper extremity hemodialysis graft or arteriovenous fistula due to this venous outflow obstruction. Endovascular intervention with percutaneous ballon angioplasty and/or stent placement has emerged as first line treatment. The fenestrated endograft as described above can be used to treat this problem. FIG. 13 illustrates the use of a fenestrated endograft to treat stenosis at the confluence of the superior vena cava and the left and right brachiocephalic veins.

Figure 14:
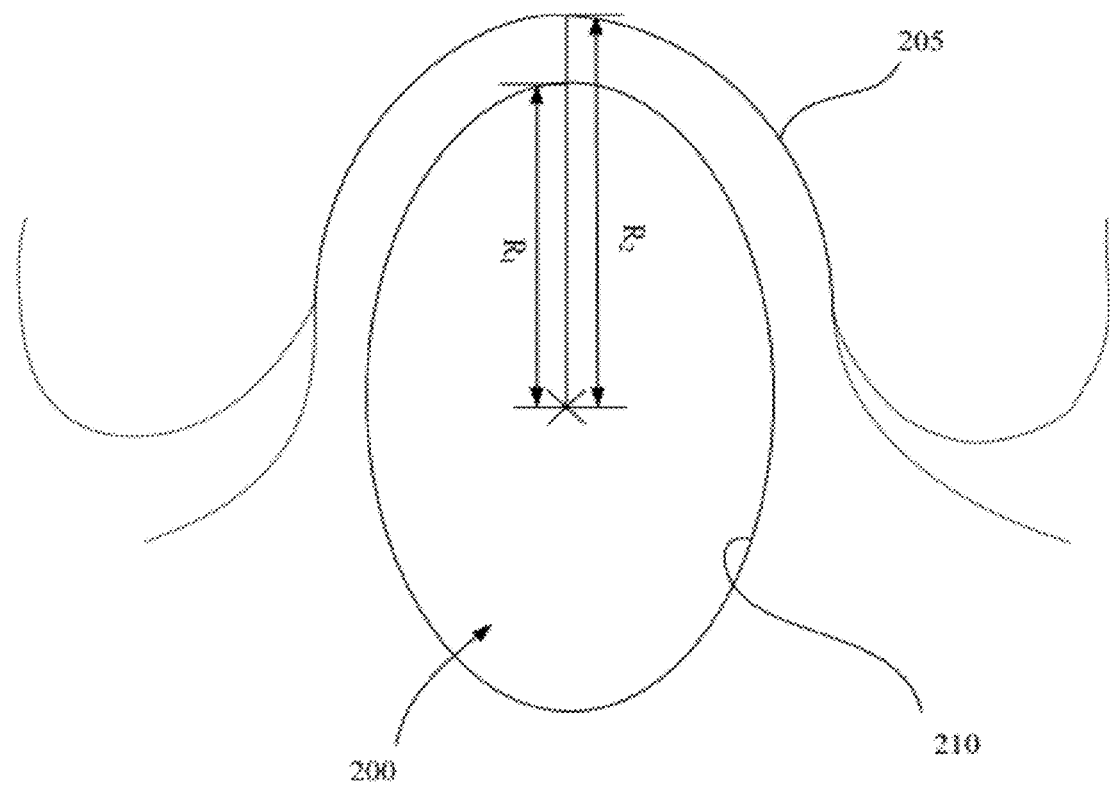
FIG. 14 illustrates schematic view of embodiments of the endograft.

FIG. 14 depicts schematic embodiments of the aperture of the endograft. In some embodiments, a fenestrated venous stent graft system is provided that includes an expandable stent frame having a proximal end portion, a distal end portion, and a central portion between the proximal and distal end portions.

In some embodiments, the elongate member has a curved segment that extends around at least one-fourth of a perimeter of the aperture. In some embodiments, the curved segment extends around at least one-third of the perimeter of the aperture. In some embodiments the curved segment extends around at least one-half of the perimeter of the aperture. The curved segment of the elongate member can provide a reinforcement for the aperture to maintain patency of the aperture when the graft stent is implanted within a patient. In some embodiments, the elongate member provides a bias force that tends to resist collapse of the aperture when the stent frame is in the expanded configuration.

The elongate member may be located adjacent a border of the aperture 200 so as to provide support for the aperture border. For example, as illustrated in FIG. 14, some embodiments provide that the elongate member has a radius of curvature $R_2$ along the curved segment 205 that closely matches a corresponding radius of curvature $R_1$ along the aperture border, or perimeter 210. In some embodiments, the curved segment 205 has a radius of curvature $R_2$ that is less than 10 percent longer than a radius of curvature $R_1$ of the corresponding perimeter 210 of the aperture 200. The corresponding perimeter of the aperture 200 is that portion of the perimeter 210 of the aperture 200 along which the curved member extends. In some embodiments, it is along about one-fourth, one-third, and one-half. In some embodiments, it is less than about one-fourth, and in some embodiments, it is more than one-half.

In some embodiments, the radius of curvature of the segment is less than 5 percent longer than the radius of curvature of the perimeter of the aperture. In some embodiments, the radius of curvature of the segment is between about 5 percent and 10 percent longer than the radius of curvature of the aperture perimeter 210. In some embodiments, the radius of curvature of the segment is greater than about 10 percent longer than the radius of curvature of the aperture perimeter 210.

Figure 15:
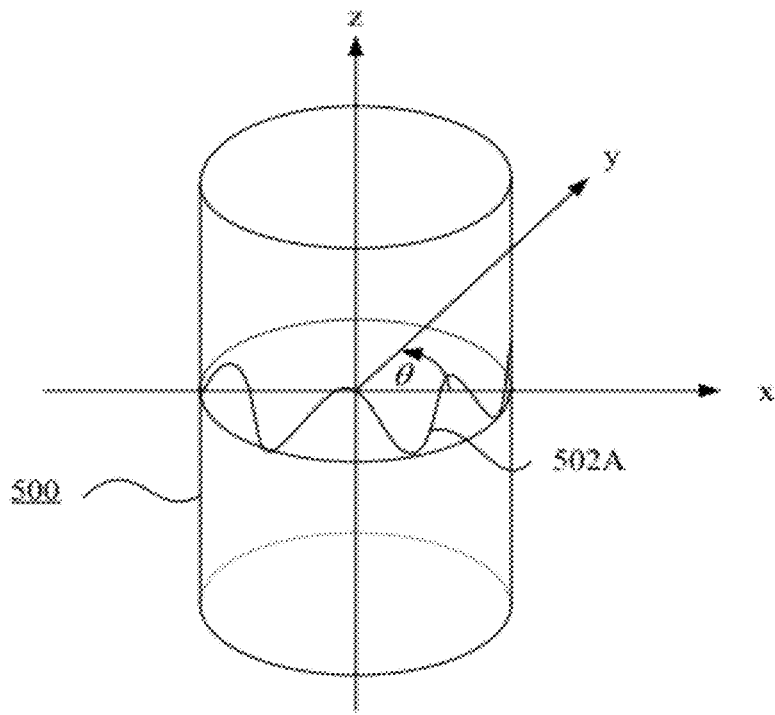
FIG. 15 illustrates the coordinates of the endograft.
Figure 16:
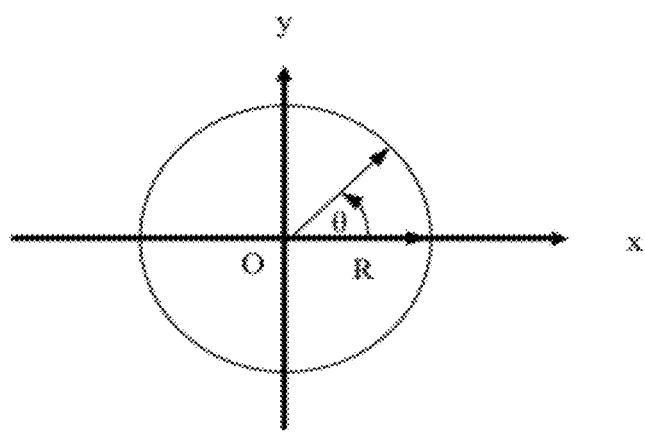
FIG. 16 illustrates the plane perpendicular to a center axis of the endograft.

The endograft, such as the penetrated endograft 500 that includes the central portion 502 of the stent frame 505 as shown in FIGS. 5A-5B, may be described in three-dimensional space with x-, y-, and z-axes. As shown in FIG. 15, the center axis of a lumen defined by the stent frame 505 extends along the z-axis. At least one sinusoidal ring or repetive-curved ring that defines the central member 502 has a radius R on the x-y plane perpendicular to the z-axis. As shown in FIGS. 14 and 15, the location of a specific point of the sinusoidal ring on the x-y plane can be defined as:

$X=R \cos(\theta)$ $Y=R \sin(\theta)$

Figure 17:
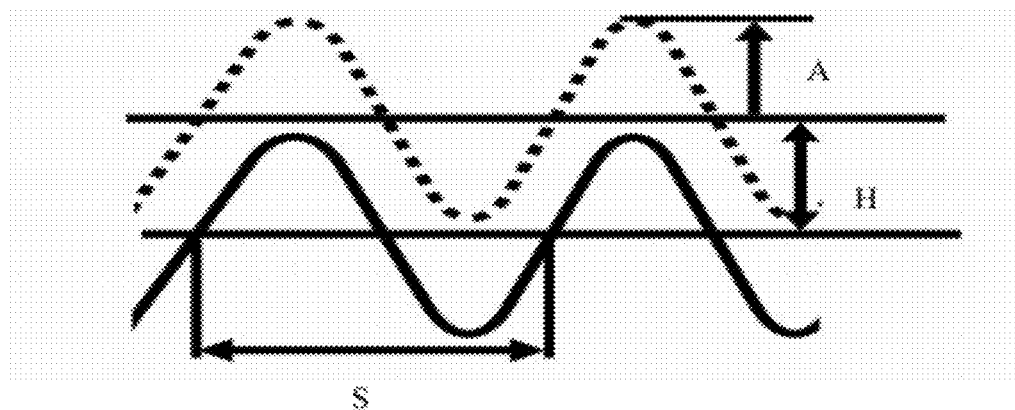
FIG. 17 illustrates an exemplary pattern or configuration of a curved segment of a central portion of the stent frame.
Figure 18:
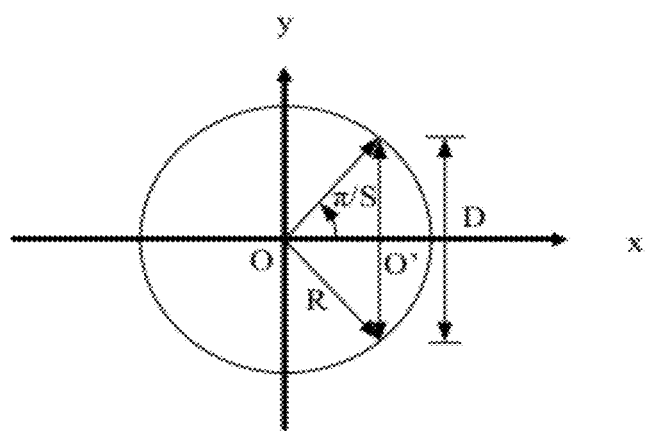
FIG. 18 illustrates the relationship between the aperture or fenestration and the configuration of the curved segment as shown in FIGS. 15-17.

The length of the central portion 502 can be determined along the z-axis. FIG. 17 shows the relationship between the amplitude A of each of the sinusoidal rings that form the central portion 502. H is the distance between two adjacent sinusoidal rings. Considering the lower sinusoidal ring is leveled at the origin O of the z-axis, the location of the upper sinusoidal ring along the z-axis can be presented by:

$Z=A \cos(S \cdot \theta)+H$

The location of the contra-lateral port, that is, the fenestration 504A at the central portion 502, can be defined with an isosceles triangle referenced from the origin of the x- and y-axes. To fix the contra-lateral port to one phase of the sinusoidal ring in the central portion 502, the maximum diameter D of the affixed portion of the contralateral port can be defined by:

$D=2R \sin(\pi/S)$.

The origin O' of the contralateral port relative to the center axis can be determined by:

$O'=R \cos(\pi/S)$.

Some embodiments of the stent graft provide that the elongate member has first and second portions, adjacent to opposite ends of the segment, respectively, that extend from the opposite ends of the segment. Some embodiments provide that the first and second portions extend from the segment in a manner that can provide support for maintaining patency of the aperture while still maintaining a degree of flexibility of the stent graft system so as to reduce the likelihood of harming tissue at the confluence.

In some embodiments, the first and second portions extend from the opposite ends of the segment with each of the first and second portions having a curvature that has a different sign than the curvature of the segment. In some embodiments, the first and second portions extend from the opposite ends of the segment with at least one of the first and second portions having a curvature that has a different sign than the curvature of the segment. The sign of the curvature relates to the second derivative of a function that defines a curve extending longitudinally along the elongate member.

For example, if the sign of the curvature of the segment is positive, in some embodiments, the curvature of the first and second portions extending from the opposite ends of the segment both could have a negative curvature when each of the first and second portions have a curvature that has a different sign than the curvature of the segment. In some embodiments then, at least one of the first and second portions of the elongate member have a curvature that is opposite the sign of the curvature of the segment, and in some embodiments, they are both opposite the sign of the curvature of the segment.

In some embodiments, a second stent graft is configured to extend a portion of the stent graft through the aperture, such that a first portion of the second stent graft is extending within and along a portion of the first stent graft and a second portion of the second stent graft is extending through the aperture and into a separate vessel than within which the first stent graft extends. Illustrated examples of this are provided, for example, in FIGS. 6A to 7. A second aperture, within the second stent graft, is preferably configured to be aligned with the lumen of the central portion of the first stent graft so as to maintain substantially unobstructed fluid communication through the first stent graft as well as the second stent graft.

Some methods implanting a stent graft system in a venous confluence include advancing into a first vessel that drains into a venous confluence, a first expandable stent frame. The frame is preferably radially expandable from a collapsed configuration to an expanded configuration and has a proximal end portion, a distal end portion, and a central portion between the proximal and distal end portions. The expandable stent has a lumen that extends through the proximal portion, central portion, and distal end portion to maintain fluid communication through the stent graft when positioned within a patient. As described above with the various embodiments, the stent graft preferably includes an aperture.

The first stent frame is expanded at the venous confluence such that one of the proximal end portion and the distal end portion resides within the first vessel and the other of the proximal end portion and the distal end portion resides at the confluence, and such that the aperture opens to a second vessel that drains into the confluence. In some embodiments, the central portion of the stent frame may includes more than one curved segments extending about a perimeter of the stent frame. These curved segments may include a plurality of sinusoidal segments as shown in FIG. 15, for example.

Some embodiments further provide, as illustrated by FIGS. 6A to 7, advancing and expanding a second stent graft into the confluence such that one of a proximal end portion and a distal end portion of the second stent graft is positioned and extends within the one of the proximal end portion and the distal end portion of the first stent graft. The second stent graft is preferably positioned such that the other of the proximal end portion and the distal end portion of the second stent graft extends through the aperture of the first stent graft and into the second vessel. In some embodiments, the second stent graft is positioned such that an aperture in a central portion of the second stent graft is aligned with the lumen of the first stent graft, to maintain fluid communication through the first stent graft.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be accomplished differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A fenestrated venous stent graft system comprising:
an expandable stent frame having a proximal end portion, a distal end portion, and a central portion between the proximal and distal end portions; and
a lumen extending through the proximal end portion, the central portion, and the distal end portion;
wherein the stent frame is radially expandable from a collapsed configuration to an expanded configuration;
wherein the central portion is coupled to a fabric that extends along a perimeter of the central portion and comprises an aperture having a cross-sectional dimension that is substantially equal to a cross-sectional dimension of an outer cross-sectional dimension of the distal portion;
wherein the central portion comprises a curved, elongate member having a curved segment that extends around at least one-fourth of a perimeter of the aperture;
wherein the segment has a radius of curvature that is less than 10 percent longer than a radius of curvature of the one-fourth of the perimeter of the aperture;
wherein the elongate member provides a bias force that tends to resist collapse of the aperture when the stent frame is in the expanded configuration;
wherein first and second portions of the elongate member, adjacent to opposite ends of the segment, respectively, each have a curvature with a different sign than the curvature of the segment.

2. The stent graft system of claim 1, wherein at least one of the first and second portions of the elongate member have a curvature that is opposite the sign of the curvature of the segment.

3. The stent graft system of claim 1, further comprising a second stent graft with a portion that is configured to extend through the aperture.

4. The stent graft system of claim 3, wherein the second stent graft comprises a second aperture that is configured to be aligned with the lumen at the central portion when the second stent graft is extended through the aperture.

5. The stent graft system of claim 1, wherein the radius of curvature of the segment is less than 5 percent longer than the radius of curvature of the one-fourth of the perimeter of the aperture.

6. The stent graft system of claim 1, wherein the radius of curvature of the segment is between about 5 percent and 10 percent longer than the radius of curvature of the one-fourth of the perimeter of the aperture.

7. The stent graft system of claim 1, wherein at least one of the first and second portions of the elongate member have a curvature that is opposite the sign of the curvature of the segment.

8. The stent graft system of claim 1, wherein the central portion of the expandable stent frame comprises a sinusoidal shape that defines at least a portion of the central portion perimeter.

9. The stent graft system of claim 1, wherein the aperture comprises a shape defined by a circle projected onto a cylinder along a line that passes through a central axis of the cylinder and at an angle relative to an axis of the cylinder.

10. The stent graft system of claim 1, wherein the expandable stent frame has a diameter, when in the expanded configuration, of between about 5 mm to about 30 mm.

11. The stent graft system of claim 1, wherein the expandable stent frame has a diameter, when in the expanded configuration, of between about 12 mm to about 24 mm.

12. The stent graft system of claim 1, wherein the expandable stent frame has a diameter, when in the collapsed configuration, of between about 2 mm to about 5 mm.

13. The stent graft system of claim 1, wherein the expandable stent frame has a diameter, when in the collapsed configuration, of between about 3 mm to about 4 mm.

14. A method of implanting a stent graft system in a venous confluence, the method comprising:
advancing, into a first vessel that drains into a venous confluence, a first expandable stent frame, radially expandable from a collapsed configuration to an expanded configuration, the first frame having a proximal end portion, a distal end portion, and a central portion between the proximal and distal end portions; the expandable stent having a lumen extending through the proximal portion, central portion, and distal end portion;
wherein the central portion is coupled to a fabric that extends along a perimeter of the central portion and comprises an aperture having a cross-sectional dimension that is substantially equal to a cross-sectional dimension of an outer cross-sectional dimension of the distal portion;
wherein the central portion comprises a curved, elongate member having a curved segment that extends around at least one-fourth of a perimeter of the aperture, and the segment has a radius of curvature that is less than 10 percent longer than a radius of curvature of the one-fourth of the perimeter of the aperture;
wherein the elongate member provides a bias force that tends to resist collapse of the aperture when the stent frame is in the expanded configuration;
wherein first and second portions of the elongate member, adjacent to opposite ends of the segment, respectively, each have a curvature with a different sign than the curvature of the segment;
expanding the first stent frame at the venous confluence such that the one of the proximal end portion and the distal end portion resides within the first vessel and the other of the proximal end portion and the distal end portion resides at the confluence, and such that the aperture opens to a second vessel that drains into the confluence.

15. The method of claim 14, further comprising advancing and expanding a second stent graft into the confluence such that one of a proximal end portion and a distal end portion of the second stent graft is positioned and extends within the one of the proximal end portion and the distal end portion of the first stent graft, and the other of the proximal end portion and the distal end portion of the second stent graft extends through the aperture of the first stent graft and into the second vessel.

16. The method of claim 15, wherein the second stent graft is positioned such that an aperture in a central portion of the second stent graft is aligned with the lumen of the first stent graft, to maintain fluid communication through the first stent graft.

17. The method of claim 15, wherein patency of the aperture of the first stent graft is maintained by expanding the second stent graft within the aperture.

18. A fenestrated venous stent graft system comprising:
a first stent frame having at least one curved segment extending about a center axis thereof, the curved segment being configured with a plurality of repetitive curves having an amplitude A along a direction of the center axis and a period S along a perimeter of the first stent frame; and a fabric extending about the center axis and the perimeter of the first stent frame, the fabric having an aperture, wherein the aperture has an origin O' relative to the center axis and a maximum diameter D determined, based on a radius R of the perimeter of the first stent frame and the period S of the repetitive curves of the curved segment, by:

$O' = R \cos(\pi/S)$ $D = 2R \sin(\pi/S)$.

19. The system of claim 18, wherein the fabric is coupled to the curved segment in a manner that forces the aperture open when the first stent frame is in an expanded configuration.

20. The system of claim 18, further comprising a second stent frame configured to extend through the aperture towards the distal or proximal end portion of the first stent frame.

21. The system of claim 18, further comprising an asymmetric radiopaque marker attached on the first stent frame or the fabric in a proximity of the aperture.

* * * * *